(12) United States Patent
Murakami et al.

(10) Patent No.: US 9,815,867 B2
(45) Date of Patent: Nov. 14, 2017

(54) PEPTIDE FOR INHIBITING VASCULAR ENDOTHELIAL GROWTH FACTOR RECEPTOR

(71) Applicants: The University of Tokyo, Tokyo (JP); Peptidream Inc., Tokyo (JP)

(72) Inventors: Hiroshi Murakami, Tokyo (JP); Takashi Kawakami, Tokyo (JP); Takahiro Ishizawa, Tokyo (JP); Hiroaki Suga, Tokyo (JP); Patrick Reid, Tokyo (JP)

(73) Assignees: The University of Tokyo, Tokyo (JP); Peptidream Inc., Tokyo (JP)

( * ) Notice: Subject to any disclaimer, the term of this patent is extended or adjusted under 35 U.S.C. 154(b) by 2 days.

(21) Appl. No.: 14/424,192

(22) PCT Filed: Sep. 2, 2013

(86) PCT No.: PCT/JP2013/073471
§ 371 (c)(1),
(2) Date: Jun. 23, 2015

(87) PCT Pub. No.: WO2014/034922
PCT Pub. Date: Mar. 6, 2014

(65) Prior Publication Data
US 2015/0299258 A1 Oct. 22, 2015

(30) Foreign Application Priority Data
Sep. 3, 2012 (JP) .................................. 2012-193453

(51) Int. Cl.
*C07K 7/08* (2006.01)
*A61K 38/00* (2006.01)

(52) U.S. Cl.
CPC ................ *C07K 7/08* (2013.01); *A61K 38/00* (2013.01)

(58) Field of Classification Search
CPC ...................................................... C07K 7/08
See application file for complete search history.

(56) References Cited

U.S. PATENT DOCUMENTS

| | | |
|---|---|---|
| 2004/0092434 A1 | 5/2004 | Betz et al. |
| 2006/0089307 A1 | 4/2006 | Kulseth |
| 2011/0319336 A1 | 12/2011 | Kawakami et al. |
| 2012/0208720 A1 | 8/2012 | Kashiwagi et al. |

FOREIGN PATENT DOCUMENTS

| | | | |
|---|---|---|---|
| JP | 2004-510784 | A | 4/2004 |
| JP | 2006-523608 | A | 10/2006 |
| JP | 2012-510287 | A | 5/2012 |
| WO | 2011049157 | A1 | 4/2011 |
| WO | 2012017256 | A2 | 2/2012 |
| WO | 2012074130 | A1 | 6/2012 |

OTHER PUBLICATIONS

Vicari et al. The Journal of Biological Chemistry vol. 286, No. 15, pp. 13612-13625, Apr. 15, 2011.*
Binetruy-Tournaire et al., "Identification of a peptide blocking vascular endothelial growth factor (VEGF)-mediated angiogenesis", Apr. 3, 2000, pp. 1525-1533, vol. 19, No. 7, Publisher: EMBO J.
Isizawa et al., "TRAP Display: A High-Speed Selection Method for the Generation of Functional Polypeptides", Mar. 18, 2013, pp. 5433-5440, vol. 135, No. 14, Publisher: J. Am. Chem. Soc. (Abstract).
Int'l Search Report received in PCT/JP2013/073471 dated Dec. 3, 2013.
"Accession No. Q5LP74", Mar. 24, 2009, Publisher: Database Uniprot [online].
Kaneko et al., "Accession No. Q89TW4", Jun. 1, 2003, Publisher: Database Uniprot [online].
Ho, et al., "Vascular endothelial growth factor: Biology and therapeutic applications", Apr. 22, 2007, p. 13491357, vol. 39, Publisher: The International Journal of Biochemistry & Cell Biology.
Scott, et al., "Antibody therapy of cancer", Apr. 1, 2012, pp. 278-287, vol. 12, Publisher: Nat. Rev. Cancer.
Shibuya, et al., "VEGF-receptor inhibitors for anti-angiogenesis", 2003, pp. 498-503, vol. 122, Publisher: Folia Pharmacol. Jpn. (English Abstract provided).
Zhang, et al., "Targeting cancer with small molecule kinase inhibitors", Jan. 1, 2009, pp. 28-39, vol. 9, Publisher: Nat. Rev. Cancer.

* cited by examiner

*Primary Examiner* — Amber D Steele
(74) *Attorney, Agent, or Firm* — Suzannah K. Sundby, Esq.; Canady + Lortz LLP

(57) ABSTRACT

An object of the present invention is to provide a VEGFR2 inhibitor peptide having high specificity and available at a low cost. The present invention provides a peptide having the following amino acid sequence:

$Xaa_1-Xaa_2-Xaa_3-Xaa_4-Xaa_5-Xaa_6-Xaa_7-Xaa_8-Xaa_9-$
$Xaa_{10}-Xaa_{11}-Xaa_{12}-Xaa_{13}-Xaa_{14}-Xaa_{15}$

[wherein, $Xaa_2$ represents Val or derivative thereof, $Xaa_6$ represents Asp or derivative thereof, $Xaa_7$ represents Pro or derivative thereof, $Xaa_8$ represents Trp or derivative thereof, $Xaa_{10}$ represents Asn or derivative thereof, $Xaa_{11}$ represents Gly or derivative thereof, $Xaa_{12}$ represents Leu or derivative thereof, $Xaa_1$, $Xaa_3$ to $Xaa_5$, $Xaa_9$, and $Xaa_{13}$ to $Xaa_{15}$ each independently represent an arbitrary amino acid or derivative thereof]; or $Xaa_{16}-Xaa_{17}-Xaa_{18}-Xaa_{19}-Xaa_{20}-Xaa_{21}-Xaa_{22}-Xaa_{23}-$
$Xaa_{24}-Xaa_{25}-Xaa_{26}-Xaa_{27}-Xaa_{28}-Xaa_{29}-Xaa_{30}$

[wherein, $Xaa_{24}$ represents His or derivative thereof, $Xaa_{25}$ represents Pro or derivative thereof, and $Xaa_{16}$ to $Xaa_{23}$ and $Xaa_{26}$ to $Xaa_{30}$ each represent an arbitrary amino acid].

8 Claims, 8 Drawing Sheets

\* Reverse sequence of BL1

FIG. 8

```
                                    Frequency
X V V V S T D P W V  N G L  W  L R C     3
X V V V S T D P W V  N G L  W  F P C     4
X V V V S T D P W V  N G L  W  F Y C     1
X V V V S T D P W V  N G L  W  L W C     1
X V V V S T D P W V  N G L  W  L Q C     1
X V V V S T D P W A  N G L  W  L A C     1
L1 X V V V S T D P W V N G L Y L D C
   1 2 3 4 5 6 7 8 9 10 11 12 13 14 15
                   Randomized residues
```

FIG. 9

```
                                          Frequency
X V  V  R H T  D P W  V N G L Y I D C        1
X V  V  V H T  D P W  V N G L Y I D C        1
X V  V  R H N  D P W  V N G L Y I D C        1
X V  V  S H P  D P W  V N G L Y I D C        2
X V  V  S H H  D P W  V N G L Y I D C        1
X V  V  K H S  D P W  V N G L Y I D C        1
X V  V  K H P  D P W  V N G L Y I D C        1
X I  V  R H P  D P W  V N G L Y I D C        1
X I  V  T H S  D P W  V N G L Y I D C        1
X V  V  T H S  D P W  V N G L Y I D C        1
X T  V  T H T  D P W  V N G L Y I D C        1
X T  V  K H T  D P W  V N G L Y I D C        1
X T  V  R H T  D P W  V N G L Y I D C        1
X T  V  Y H S  D P W  V N G L Y I D C        1
L1 X V V V S T D P W V N G L Y L D C
   1 2 3 4 5 6 7 8 9 10 11 12 13 14 15
                 Randomized residues
```

FIG. 10

|  |  |  |  |  |  |  |  |  |  |  |  |  |  |  | Frequency |
|---|---|---|---|---|---|---|---|---|---|---|---|---|---|---|---|
| X | T | V | S | H | P | D | P | W | V | N | G | L | W | I | R | C | 1 |
| X | T | V | Y | H | P | D | P | W | V | N | G | L | W | I | R | C | 1 |
| X | T | V | W | H | P | D | P | W | V | N | G | L | W | I | Y | C | 1 |
| X | E | V | K | H | P | D | P | W | V | N | G | L | W | I | Y | C | 1 |
| X | T | V | V | H | P | D | P | W | V | N | G | L | W | I | S | C | 1 |
| X | T | V | R | H | P | D | P | W | V | N | G | L | W | L | S | C | 1 |
| X | T | V | R | H | P | D | P | W | V | N | G | L | W | F | S | C | 1 |
| X | T | V | S | H | P | D | P | W | V | N | G | L | W | L | Q | C | 1 |
| X | T | V | T | H | P | D | P | W | V | N | G | L | W | L | P | C | 2 |
| X | T | V | T | H | P | D | P | W | V | N | G | L | Y | L | P | C | 1 |
| X | T | V | Y | H | P | D | P | W | V | N | G | L | W | L | P | C | 1 |
| X | T | V | V | H | P | D | P | W | V | N | G | L | W | L | P | C | 1 |
| X | T | V | F | H | P | D | P | W | V | N | G | L | W | I | P | C | 1 |
| X | A | V | T | H | S | D | P | W | V | N | G | L | W | L | P | C | 1 |
| X | T | V | T | H | S | D | P | W | V | N | G | L | W | F | P | C | 1 |
| X | E | V | S | H | P | D | P | W | V | N | G | L | W | F | P | C | 1 |
| X | A | V | S | H | P | D | P | W | V | N | G | L | W | F | P | C | 1 |
| X | S | V | V | H | H | D | P | W | V | N | G | L | W | F | P | C | 1 |
| L1 | X | V | V | V | S | T | D | P | W | V | N | G | L | Y | L | D | C |

1 2 3 4 5 6 7 8 9 10 11 12 13 14 15

Randomized residues

FIG. 11

```
                                    Frequency
      X I G H Y R V K V H P I S L A P C    1
      X I G R Y R V K V H P I S L A P C    1
      X I G H Y R V K V H P I S L S P C    1
      X I G P Y R V K V H P I S L E P C    1
      X I G H Y R V K V H P I S L E P C    1
      X I G H Y R V K V H P I S L E Y C    1
      X I G H Y R V K V H P I S L E W C    1
      X I G H Y R V K V H P I S L L P C    1
      X I G H Y R V K V H P V S L E P C    3
      X I G H Y R V K V H P V S F E P C    1
      X I G H Y R V K V H P V S L E S C    1
      X I G D Y R V K V H P V S L E Y C    1
      X I G H Y R V K V H P V T L A W C    1
      X V G H Y R V K V H P V G L W P C    1
BL1   X I G H Y R V K V H P I S L E R C
      16 17 18 19 20 21 22 23 24 25 26 27 28 29 30
                    Randomized residues
```

FIG. 12

```
                                    Frequency
      X V N G Y R V K V H P I S L E R C    1
      X V N G Y S I K V H P I S L E R C    1
      X I N G Y K I K V H P I S L E R C    1
      X I G P Y K I R V H P I S L E R C    1
      X I G P Y R I R L H P I S L E R C    1
      X Y G P Y A I K V H P I S L E R C    1
      X I G P Y V I K V H P I S L E R C    1
      X I G R F R I K V H P I S L E R C    1
      X L G R W S I K V H P I S L E R C    1
      X I G S F V I R V H P I S L E R C    1
      X I R G F R I R V H P I S L E R C    1
      X V G P Y R I R V H P I S L E R C    1
      X V G I Y Q I R V H P I S L E R C    1
      X I G H Y R V K V H P V S L E Y C    1
BL1   X I G H Y R V K V H P I S L E R C
      16 17 18 19 20 21 22 23 24 25 26 27 28 29 30
      Randomized residues
```

FIG. 13

|  |  |  |  |  |  |  |  |  |  |  |  |  |  |  | Frequency |
|---|---|---|---|---|---|---|---|---|---|---|---|---|---|---|---|
| X | L | Y | G | Y | R | V | K | V | H | P | I | S | L | E | P | C | 1 |
| X | I | G | I | Y | R | V | K | V | H | P | I | S | L | E | P | C | 1 |
| X | I | G | P | Y | R | V | K | V | H | P | I | S | L | E | P | C | 4 |
| X | I | G | P | Y | W | V | K | V | H | P | I | S | L | E | P | C | 1 |
| X | I | G | P | Y | R | V | K | V | H | P | V | S | L | E | P | C | 4 |
| X | I | G | P | Y | R | I | K | V | H | P | V | S | L | E | P | C | 1 |
| X | V | G | P | Y | R | V | K | V | H | P | V | S | L | E | P | C | 1 |
| X | I | G | P | Y | V | V | K | V | H | P | V | S | L | E | P | C | 1 |
| X | I | G | P | Y | R | V | K | V | H | P | V | S | L | E | Y | C | 1 |
| X | I | G | P | Y | W | V | K | V | H | P | V | S | L | E | W | C | 5 |
| X | I | N | G | Y | Y | V | K | V | H | P | V | S | L | D | W | C | 1 |

BL1  *X  I  G  H  Y  R  V  K  V  H  P  I  S  L  E  R  C*
     16 17 18 19 20 21 22 23 24 25 26 27 28 29 30

Randomized residues

PEPTIDE FOR INHIBITING VASCULAR ENDOTHELIAL GROWTH FACTOR RECEPTOR

RELATED APPLICATION DATA

This application is a 371 of PCT/JP2013/073471, filed Sep. 2, 2013, which claims priority to JP 2012-193453, filed Sep. 3, 2012, and are herein incorporated by reference in their entirety.

REFERENCE TO A SEQUENCE LISTING SUBMITTED VIA EFS-WEB

The content of the ASCII text file of the sequence listing named "20170815_034574_005US1_subseq_ST25", which is 82.9 kb in size was created on Aug. 15, 2017 and electronically submitted via EFS-Web on Aug. 17, 2017, is incorporated herein by reference in its entirety

TECHNICAL FIELD

The present invention relates to a peptide inhibiting the activity of a vascular endothelial growth factor receptor (VEGFR2), and the like.

BACKGROUND ART

For the growth of malignant tumors, oxygen and nutrition are necessary. Malignant tumors therefore secrete a vascular endothelial growth factor (VEGF) and the like to cause angiogenesis for themselves. Inhibition of angiogenesis is presumed to suppress growth or malignant transformation of tumors so that there have been proposed various molecular targeting therapies with VEGF or VEGFR2, a receptor of vascular endothelial growth factor, as a target.

VEGFR2 is composed of an extracellular domain, a transmembrane domain, and an intracellular tyrosine kinase domain and it interacts with VEGF through the extracellular domain. VEGFR2, when a dimer VEGF binds thereto, dimerizes and is activated through auto-phosphorylation by the intracellular tyrosine kinase domain. The activation of VEGFR2 causes migration, growth, and survival of cells, resulting in angiogenesis. Inhibition of interaction between VEGF and VEGFR2 or signaling caused thereby is presumed to be clinically useful because it can suppress pathological angiogenesis such as retinal angiopathy as well as malignant tumors (refer to, for example, Non-patent Documents 1 to 4).

In practice, anti-VEGF neutralizing antibodies, anti-VEGFR2 neutralizing antibodies, and compounds inhibiting VEGFR2 phosphorylation have been under development and some of them have already been industrialized (refer to the above-mentioned Non-patent Document 1). Anti-VEGF antibodies have been verified to exhibit a certain effect when used in combination with chemotherapy; however, they are expensive and are required to have a low molecular weight. A small-molecule inhibitor against phosphorylation of VEGFR2 has already been developed, but it still has a problem in specificity.

CITATION LIST

Non-Patent Documents

[Non-patent Document 1] Masabumi Shibuya, Nippon Yakurigaku Zasshi (Folia Pharmacol. Jpn.), 122, 498-503 (2003)

[Non-patent Document 2] Q. T. Ho, et al., Int. J. Biochem. Cell Biol., 39, 1349-57 (2007)

[Non-patent Document 3] Zhang, J., et al., Nat. Rev. Cancer, 9, 28-39 (2008)

[Non-patent Document 4] Scott, A. M., et al., Nat. Rev. Cancer, 12, 278-87 (2012)

SUMMARY OF THE INVENTION

Problem to be Solved by the Invention

An object of the present invention is to provide a VEGFR2 inhibitor peptide that strongly binds to VEGFR2 with high specificity and thereby inhibits its function, and can be produced at a low cost.

Means for Solving the Problem

The present inventors have proceeded with research in order to overcome the above-mentioned problem, which results in rinding a peptide having high affinity with VEGFR2, and have verified that administration of the peptide to vascular endothelial cells expressing VEGFR2 prevents phosphorylation of VEGFR2, markedly suppresses growth of vascular endothelial cells, and has a tendency to suppress angiogenesis. Lastly, they have optimized the sequence of the peptide and completed the present invention.

The present invention therefore relates to:

(SEQ ID NO: 140)
$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}Xaa_{11}\text{-}Xaa_{12}\text{-}Xaa_{13}\text{-}Xaa_{14}\text{-}Xaa_{15}$

[wherein, $Xaa_2$ represents Val or a derivative thereof, $Xaa_6$ represents Asp or a derivative thereof, $Xaa_7$ represents Pro or a derivative thereof, $Xaa_8$ represents Trp or a derivative thereof, $Xaa_{10}$ represents Asn or a derivative thereof, $Xaa_{11}$ represents Gly or a derivative thereof, $Xaa_{12}$ represents Leu or a derivative thereof, and $Xaa_1$, $Xaa_3$ to $Xaa_5$, $Xaa_9$, and $Xaa_{13}$ to $Xaa_{15}$ each independently represents an arbitrary amino acid or a derivative thereof];

[2] the peptide as described above in [1],
wherein $Xaa_1$ represents an arbitrary amino acid or a derivative thereof,
$Xaa_3$ represents an arbitrary amino acid or a derivative thereof,
$Xaa_4$ is selected from Gly, His, and Ser, and derivatives thereof,
$Xaa_5$ represents an arbitrary amino acid or a derivative thereof,
$Xaa_9$ is selected from aliphatic amino acids and derivatives thereof,
$Xaa_{13}$ represents an arbitrary amino acid or a derivative thereof,
$Xaa_{14}$ is selected from hydrophobic amino acids and derivatives thereof, and
$Xaa_{15}$ represents an arbitrary amino acid or a derivative thereof;

[3] the peptide as described above in [1] or [2], wherein $Xaa_1$ is selected from Val and Thr, and derivatives thereof,
$Xaa_3$ represents an arbitrary amino acid or a derivative thereof,
$Xaa_4$ represents His or a derivative thereof,
$Xaa_5$ represents an arbitrary amino acid or a derivative thereof, Xaa$_9$ represents Val or a derivative thereof, Xaa$_{13}$ represents an aromatic amino acid or a derivative thereof, Xaa$_{14}$ is selected from Phe, Leu, and Ile and derivatives thereof, and Xaa$_{15}$ is selected from Pro and Ser and derivatives thereof;

[4] the peptide as described above in any one of [1] to [3], wherein Xaa$_1$-Xaa$_2$-Xaa$_3$-Xaa$_4$-Xaa$_5$-Xaa$_6$-Xaa$_7$-Xaa$_8$ (SEQ ID NO: 141) is selected from the group consisting of VVRHTDPW (SEQ ID NO: 1), VVVHTDPW (SEQ ID NO: 2), VVRHNDPW (SEQ ID NO: 3), VVSHPDPW (SEQ ID NO: 4), VVSHHDPW (SEQ ID NO: 5), VVKHSDPW (SEQ ID NO: 6), VVKHPDPW (SEQ ID NO: 7), IVRHPDPW (SEQ ID NO: 8), IVTHSDPW (SEQ ID NO: 9), VVTHSDPW (SEQ ID NO: 10), TVTHTDPW (SEQ ID NO: 11), TVKHTDPW (SEQ ID NO: 12), TVRHTDPW (SEQ ID NO: 13), TVYHSDPW (SEQ ID NO: 14), and VVVSTDPW (SEQ ID NO: 15);

[5] the peptide as described above in any one of [1] to [4], wherein Xaa$_9$-Xaa$_{10}$-Xaa$_{11}$-Xaa$_{12}$-Xaa$_{13}$-Xaa$_{14}$-Xaa$_{15}$ (SEQ ID NO: 229) is selected from the group consisting of VNGLWLR (SEQ ID NO: 16), VNGLWFP (SEQ ID NO: 17), VNGLWFY (SEQ ID NO: 18), VNGLWLW (SEQ ID NO: 19), VNGLWLQ (SEQ ID NO: 20), ANGLWLA (SEQ ID NO: 21), and VNGLYLD (SEQ ID NO: 22);

[6] the peptide as described above in [1], wherein Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$ (SEQ ID NO: 140) is selected from the group consisting of HVTHQDPWVNGLWIA (SEQ ID NO: 23), VVSHHDPWVNGLFIA (SEQ ID NO: 24), VVVHADPWVNGLWIQ (SEQ ID NO: 25), VVKHPDPWVNGLYFH (SEQ ID NO: 26), VVQHRDPWVNGLWFP (SEQ ID NO: 27), SVVHSDPWVNGLYLS (SEQ ID NO: 28), AVKHSDPWVNGLYLP (SEQ ID NO: 29), SVTHIDPWVNGLYLP (SEQ ID NO: 30), KVSHFDPWVNGLWLP (SEQ ID NO: 31), TVTHRDPWVNGLILS (SEQ ID NO: 32), QVSHPDPWVNGLILQ (SEQ ID NO: 33), TVYSDDPWVNGLWLR (SEQ ID NO: 34), SVYGLDPWINGLRFV (SEQ ID NO: 35), TVFHTDPWVNGLWIS (SEQ ID NO: 36), TVRHTDPWVNGLWIS (SEQ ID NO: 37), TVKHPDPWVNGLWIS (SEQ ID NO: 38), TVTHSDPWVNGLFLP (SEQ ID NO: 39), VVTHPDPWVNGLFLP (SEQ ID NO: 40), TVTHIDPWVNGLWLP (SEQ ID NO: 41), TVVHADPWVNGLYLP (SEQ ID NO: 42), TVVHSDPWVNGLWLP (SEQ ID NO: 43), TVIHPDPWVNGLWLP (SEQ ID NO: 44), IVSHPDPWVNGLWLP (SEQ ID NO: 45), SVSHPDPWVNGLWLP (SEQ ID NO: 46), EVSHPDPWVNGLWIP (SEQ ID NO: 47), IVYHADPWVNGLWLS (SEQ ID NO: 48), VVRHSDPWVNGLWID (SEQ ID NO: 49), VVYSSDPWVNGLHLT (SEQ ID NO: 50), TVSHPDPWVNGLWIR (SEQ ID NO: 51), TVYHPDPWVNGLWIR (SEQ ID NO: 52), TVWHPDPWVNGLWIY (SEQ ID NO: 53), EVKHPDPWVNGLWIY (SEQ ID NO: 54), TVVHPDPWVNGLWIS (SEQ ID NO: 55), TVRHPDPWVNGLWLS (SEQ ID NO: 56), TVRHPDPWVNGLWFS (SEQ ID NO: 57), TVSHPDPWVNGLWLQ (SEQ ID NO: 58), TVHPDPWVNGLWLP (SEQ ID NO: 59), TVTHPDPWVNGLYLP (SEQ ID NO: 60), TVYHPDPWVNGLWLP (SEQ ID NO: 61), TVVHPDPWVNGLWLP (SEQ ID NO: 62), TVFHPDPWVNGLWIP (SEQ ID NO: 63), AVTHSDPWVNGLWLP (SEQ ID NO: 64), TVTHSDPWVNGLWFP (SEQ ID NO: 65), EVSHPDPWVNGLWFP (SEQ ID NO: 66), AVSHPDPWVNGLWFP (SEQ ID NO: 67), and SVVHHDPWVNGLWFP (SEQ ID NO: 68);

[7] a peptide having an amino acid sequence obtained by deleting, adding, or substituting one or several amino acids in the amino acid sequence of the peptide as described above any one of [1] to [6] and having inhibiting activity against a vascular endothelial growth factor receptor VEGFR2;

[8] a peptide comprising the following amino acid sequence: Xaa$_{16}$-Xaa$_{17}$-Xaa$_{18}$-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Xaa$_{29}$-Xaa$_{30}$ (SEQ ID NO: 142)

[wherein, Xaa$_{24}$ represents His or a derivative thereof, Xaa$_{25}$ represents Pro or a derivative thereof, and Xaa$_{16}$ to Xaa$_{23}$ and Xaa$_{26}$ to Xaa$_{30}$ each represent an arbitrary amino acid];

[9] the peptide as described above in [8], wherein Xaa$_{16}$ is selected from hydrophobic amino acids and derivatives thereof, Xaa$_{17}$ represents an arbitrary amino acid or a derivative thereof, Xaa$_{18}$ represents an arbitrary amino acid or a derivative thereof, Xaa$_{19}$ represents an aromatic amino acid or a derivative thereof, Xaa$_{20}$ represents an arbitrary amino acid or a derivative thereof, Xaa$_{21}$ is selected from hydrophobic aliphatic amino acids and derivatives thereof, Xaa$_{22}$ is selected from amino acids having a positive charge and derivatives thereof, Xaa$_{23}$ is selected from hydrophobic aliphatic amino acids and derivatives thereof, Xaa$_{26}$ is selected from hydrophobic aliphatic amino acids and derivatives thereof, Xaa$_{27}$ is selected from hydrophilic amino acids having no charge and derivatives thereof, Xaa$_{28}$ is selected from hydrophobic amino acids and derivatives thereof, Xaa$_{29}$ represents an arbitrary amino acid or a derivative thereof, and Xaa$_{30}$ represents an arbitrary amino acid or a derivative thereof;

[10] the peptide as described above in [8] or [9], wherein Xaa$_{16}$ is selected from Ile and Val and derivatives thereof, Xaa$_{17}$ is selected from Gly and Asn and derivatives thereof, Xaa$_{18}$ represents an arbitrary amino acid or a derivative thereof, Xaa$_{19}$ is selected from aromatic amino acids and derivatives thereof, Xaa$_{20}$ represents an arbitrary amino acid or a derivative thereof, Xaa$_{21}$ is selected from Ile and Val and derivatives thereof, Xaa$_{22}$ is selected from Lys and Arg, and derivatives thereof, Xaa$_{23}$ represents Val or a derivative thereof, Xaa$_{26}$ is selected from Ile and Val and derivatives thereof, Xaa$_{27}$ represents Ser or a derivative thereof, Xaa$_{28}$ represents Leu or a derivative thereof, Xaa$_{29}$ represents Glu or a derivative thereof, and Xaa$_{30}$ represents Pro or an aromatic amino acid or a derivative thereof;

[11] the peptide as described above in any one of [7] to [9], wherein Xaa$_{16}$-Xaa$_{17}$-Xaa$_{18}$-Xaa$_{19}$-Xaa$_{20}$-Xaa$_{21}$-Xaa$_{22}$-Xaa$_{23}$ (SEQ ID NO: 230) is selected from the group consisting of VNGYRVKV (SEQ ID NO: 69), VNGYSIKV (SEQ ID NO: 70), INGYKIKV (SEQ ID NO: 71), IGPYKIRV (SEQ ID NO: 72), IGPYRIRL (SEQ ID NO: 73), YGPYAIKV (SEQ ID NO: 74), IGPYVIKV (SEQ ID NO: 75), IGRFRIKV (SEQ ID NO: 76), LGRWSIKV (SEQ ID NO: 77), IGSFVIRV (SEQ ID NO: 78), IRGFRIRV (SEQ ID NO: 79), VGPYRIRV (SEQ ID NO: 80), VGIYQIRV (SEQ ID NO: 81), IGHYRVKV (SEQ ID NO: 82), and IGHYRVKV (SEQ ID NO: 83);

[12] the peptide as described above in any one of [8] to [11], wherein $Xaa_{24}$-$Xaa_{25}$-$Xaa_{26}$-$Xaa_{27}$-$Xaa_{28}$-$Xaa_{29}$-$Xaa_{30}$ (SEQ ID NO: 231) is selected from the group consisting of HPISLAP (SEQ ID NO: 84), HPISLSP (SEQ ID NO: 85), HPISLEP (SEQ ID NO: 86), HPISLEY (SEQ ID NO: 87), HPISLEW (SEQ ID NO: 88), HPISLLP (SEQ ID NO: 89), HPVSLEP (SEQ ID NO: 90), HPVSFEP (SEQ ID NO: 91), HPVSLES (SEQ ID NO: 92), HPVSLEY (SEQ ID NO: 93), HPVTLAW (SEQ ID NO: 94), HPVGLWP (SEQ ID NO: 95), and HPISLER (SEQ ID NO: 96);

[13] the peptide as described above in [8], wherein $Xaa_{16}$-$Xaa_{17}$-$Xaa_{18}$-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$Xaa_{27}$-$Xaa_{28}$-$Xaa_{29}$-$Xaa_{30}$ (SEQ ID NO: 142) is selected from the group consisting of LNGYYVKVHPVSLEP (SEQ ID NO: 97), LNGYRVKVHPISLEP (SEQ ID NO: 98), VGPYAVKVHPISLSP (SEQ ID NO: 99), VGHYRVKVHPISLLP (SEQ ID NO: 100), IGAYKVKVHPISLQP (SEQ ID NO: 101), LGPYRVKVHPISLHF (SEQ ID NO: 102), IGPYLVKVHPVSLHF (SEQ ID NO: 103), IGEYRVKVHPISLAP (SEQ ID NO: 104), IGPYRVKVHPVSLLP (SEQ ID NO: 105), IGIYRVKVHPVSLEP (SEQ ID NO: 106), IGPYAVKVHPVSLEP (SEQ ID NO: 107), IGTWVVKVHPVSLEP (SEQ ID NO: 108), INSYVVKVHPISLEP (SEQ ID NO: 109), ILGYFVKVHPVSLDP (SEQ ID NO: 110), YNGFAVKVHPISLEN (SEQ ID NO: 111), VNGYAVKVHPVSLEP (SEQ ID NO: 112), VNGYIVKVHPVSLEP (SEQ ID NO: 113), IYGFAVKVHPVSLEP (SEQ ID NO: 114), IGIYRVKVHPISLEY (SEQ ID NO: 115), IGIFRVKVHPISLEP (SEQ ID NO: 116), IGIYRVKVHPISLEP (SEQ ID NO: 117), IGRYAVKVHPISLEP (SEQ ID NO: 118), IGPYWVKVHPISLLP (SEQ ID NO: 119), IGPYHVKVHPVSLEP (SEQ ID NO: 120), IGPWFVKVHPVSLEP (SEQ ID NO: 121), IGPYRVKVHPVSLEY (SEQ ID NO: 122), IGPYRVKVHPISLEW (SEQ ID NO: 123), VNGYRVKVHPISLDW (SEQ ID NO: 124), LYGYRVKVHPISLEP (SEQ ID NO: 125), IGIYRVKVHPISLEP (SEQ ID NO: 126), IGPYRVKVHPISLEP (SEQ ID NO: 127), IGPYWVKVHPISLEP (SEQ ID NO: 128), IGPYRVKVHPVSLEP (SEQ ID NO: 129), IGPYRIKVHPVSLEP (SEQ ID NO: 130), VGPYRVKVHPVSLEP (SEQ ID NO: 131), IGPYVVKVHPVSLEP (SEQ ID NO: 132), IGPYRVKVHPVSLEY (SEQ ID NO: 133), IGPYWVKVHPVSLEW (SEQ ID NO: 134), and INGYYVKVHPVSLDW (SEQ ID NO: 135);

[14] a peptide having an amino acid sequence obtained by deleting, adding, or substituting one or several amino acids in the amino acid sequence of the peptide as described above any one of [8] to [13] and having inhibiting activity against a vascular endothelial growth factor receptor VEGFR2; and

[15] a drug containing the peptide as described above in any one of [1] to [14].

Effect of the Invention

The peptide according to the present invention can inhibit an interaction between VEGF and VEGFR2 and suppress angiogenesis. The peptide according to the present invention is therefore presumed to be useful for prevention or treatment of diseases that involve pathological angiogenesis, for example, malignant tumor, diabetic retinopathy, rheumatoid arthritis, and arteriosclerosis. The peptide according to the present invention is presumed to have fewer side effects because it binds to VEGFR2 with high specificity. In addition, it can be produced at a low cost compared with a protein drug. Angiogenesis can be inhibited more strongly by using the peptide of the present invention in combination with a drug having another mechanism of action such as phosphorylation inhibitor.

BRIEF DESCRIPTION OF THE DRAWINGS

FIG. 8 shows the amino acid sequence of peptides selected as a result of constructing a library in which $Xaa_9$ to $Xaa_{15}$ of the peptide sequence of L1 have been randomized and selecting the sequence that binds to VEGFR2 by TRAP display method. The sequences from top to bottom are SEQ ID NO: 146 to SEQ ID NO: 152.

FIG. 9 shows the amino acid sequence of peptides selected as a result of constructing a library in which $Xaa_1$ to $Xaa_8$ of the peptide sequence of L1 have been randomized and selecting the sequence that binds to VEGFR2 by TRAP display method. The sequences from top to bottom are SEQ ID NO: 153 to SEQ ID NO: 167.

FIG. 10 shows the amino acid sequence of peptides selected as a result of constructing a library in which $Xaa_1$, $Xaa_3$ to $Xaa_5$, $Xaa_9$, and $Xaa_{13}$ of the peptide sequence of L1 have been randomized and selecting the sequence that binds to VEGFR2 by TRAP display method. The sequences from top to bottom are SEQ ID NO: 168 to SEQ ID NO: 186.

FIG. 11 shows the amino acid sequence of peptides selected as a result of constructing a library in which $Xaa_{24}$ to $Xaa_{30}$ of the peptide sequence of BL1 have been randomized and selecting the sequence that binds to VEGFR2 by TRAP display method. The sequences from top to bottom are SEQ ID NO: 187 to SEQ ID NO: 201.

FIG. 12 shows the amino acid sequence of peptides selected as a result of constructing a library in which $Xaa_{16}$ to $Xaa_{23}$ of the peptide sequence of BL1 have been randomized and selecting the sequence that binds to VEGFR2 by TRAP display method. The sequences from top to bottom are SEQ ID NO: 202 to SEQ ID NO: 216.

FIG. 13 shows the amino acid sequence of peptides selected as a result of constructing a library in which $Xaa_{16}$ to $Xaa_{20}$, $Xaa_{26}$, $Xaa_{29}$, and $Xaa_{30}$ of the peptide sequence of BL1 have been randomized and selecting the sequence that binds to VEGFR2 by TRAP display method. The sequences from top to bottom are SEQ ID NO: 217 to SEQ ID NO: 228.

MODE FOR CARRYING OUT THE INVENTION

Figure 1A:
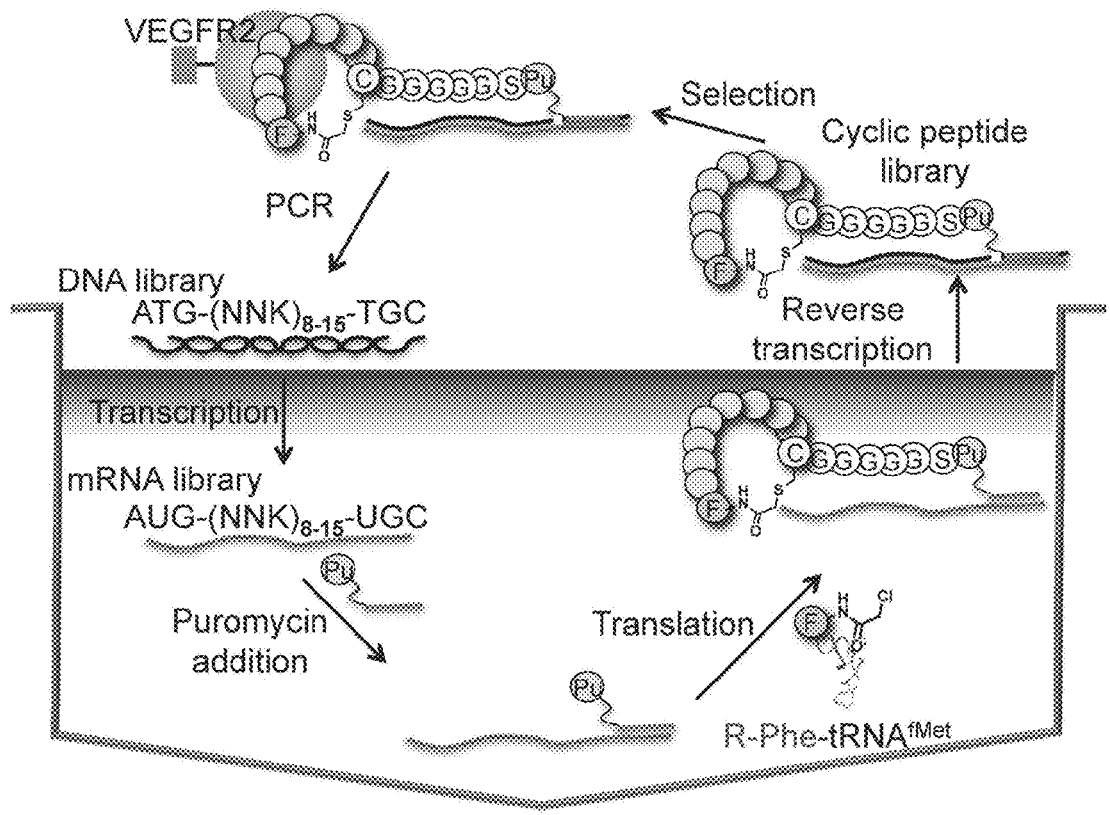
FIG. 1A shows the outline of TRAP display method that was used for selecting a VEGFR2-binding cyclic peptide. In this figure, Pu represents puromycin. The cyclic peptide library sequence is SEQ ID NO: 143, the DNA library sequence is SEQ ID NO: 144, and the mRNA library sequence is SEQ ID NO: 145.

In one aspect of the present invention, the peptide contains 15 amino acids represented by the following formula [I]:

[I]                                              (SEQ ID NO: 140)

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-

$Xaa_{11}$-$Xaa_{12}$-$Xaa_{13}$-$Xaa_{14}$-$Xaa_{15}$ ...

wherein, $Xaa_2$ represents Val or a derivative thereof, $Xaa_6$ represents Asp or a derivative thereof, $Xaa_7$ represents Pro or a derivative thereof, $Xaa_8$ represents Trp or a derivative thereof, $Xaa_{10}$ represents Asn or a derivative thereof, $Xaa_{11}$ represents Gly or a derivative thereof, $Xaa_{12}$ represents Leu or a derivative thereof, and $Xaa_1$, $Xaa_3$ to $Xaa_5$, $Xaa_9$, and $Xaa_{13}$ to $Xaa_{15}$ each represent an arbitrary amino acid or a derivative thereof.

The term "amino acid or a derivative thereof" is used herein in the broadest sense and includes artificial amino acid variants and derivatives as well as natural amino acids. Amino acids may be indicated by conventionally-used one-letter code or three-letter code. Examples of the amino acid or a derivative thereof used herein include natural proteinogenic L-amino acids, nonnatural amino acids; and chemically synthesized compounds having properties known in the art as characteristics of an amino acid. Examples of the nonnatural amino acids include, but not limited to, amino acids having a main chain structure different from that of natural amino acids such as α,α-disubstituted amino acids (such as α-methylalanine), N-alkyl-α-amino acids, D-amino acids, β-amino acids, and α-hydroxy acids; amino acids having a side-chain structure different from that of natural amino acids (such as norleucine and homohistidine); amino acid having extra methylene in the side chain thereof (such as "homo" amino acids, homophenylalanine, and homohistidine); and amino acids obtained by substituting a carboxylic acid functional group in the side chain thereof by a sulfonic acid group (such as cysteinic acid).

In the formula [I], $Xaa_2$ represents Val or a derivative thereof, $Xaa_6$ represents Asp or a derivative thereof, $Xaa_7$ represents Pro or a derivative thereof, $Xaa_8$ represents Trp or a derivative thereof, $Xaa_{10}$ represents Asn or a derivative thereof, $Xaa_{11}$ represents Gly or a derivative thereof, and $Xaa_{12}$ represents Leu or a derivative thereof.

As will be shown later in Examples, the present inventors have found that a peptide represented by the following formula:

(SEQ ID NO: 136)

ClAc-L-Phe-Val-Val-Val-Ser-Thr-Asp-Pro-Trp-Val-

Asn-Gly-Leu-Tyr-Ile-Asp-Cys (which will hereinafter be called "L1") strongly binds to VEGFR2 with high specificity and thereby inhibits its function. As a result of optimization of the sequence from the standpoint of a binding property to VEGFR2, it has been verified that $Xaa_2$, $Xaa_6$, $Xaa_7$, $Xaa_8$, $Xaa_{10}$, $Xaa_{11}$, and $Xaa_{12}$ each represent the same amino acid in any peptide before and after optimization. These seven amino acids are therefore presumed to be particularly important among 15 amino acids in binding to VEGFR2.

The other amino acid residues, that is, $Xaa_1$, $Xaa_3$ to $Xaa_5$, $Xaa_9$, and $Xaa_{13}$ to $Xaa_{15}$ are independently selected from arbitrary amino acids and derivatives thereof.

The $Xaa_1$, $Xaa_3$ to $Xaa_5$, $Xaa_9$, and $Xaa_{13}$ to $Xaa_{15}$ are preferably selected from compounds having the following characteristics.

$Xaa_1$: any amino acid or a derivative thereof, particularly, Val or Thr.

$Xaa_3$: any amino acid or a derivative thereof.

$Xaa_4$: His, Ser, or Gly, or a derivative thereof, particularly His.

$Xaa_5$: any amino acid or a derivative thereof, particularly, Ser, Thr, or Pro.

$Xaa_9$: an aliphatic amino acid or a derivative thereof such as Val, Ala, or Ile, particularly, Val.

$Xaa_{13}$: any amino acid or a derivative thereof, particularly, an aromatic amino acid.

$Xaa_{14}$: a hydrophobic amino acid or a derivative thereof, such as Leu, Phe, or Ile.

$Xaa_{15}$: any amino acid or a derivative thereof, particularly, Pro or Ser.

The above-described characteristics of the $Xaa_1$, $Xaa_3$ to $Xaa_5$, $Xaa_9$, and $Xaa_{13}$ to $Xaa_{15}$ are those found both in the sequence of L1 that binds to VEGFR2 and thereby inhibits the activity thereof and in the optimized sequence of it so that a peptide having any of the above-described characteristics is presumed to have a very high possibility of having VEGFR2 inhibiting activity similar to L1.

In the peptide represented by the formula [I], $Xaa_1$-$Xaa_2$-$Xaa_3$-$Xaa_4$-$Xaa_5$-$Xaa_6$-$Xaa_7$-$Xaa_8$ (SEQ ID NO: 141) may be selected from the group consisting of VVRHTDPW (SEQ ID NO: 1), VVVHTDPW (SEQ ID NO: 2), VVRHNDPW (SEQ ID NO: 3), VVSHPDPW (SEQ ID NO: 4), VVSHHDPW (SEQ ID NO: 5), VVKHSDPW (SEQ ID NO: 6), VVKHPDPW (SEQ ID NO: 7), IVRHPDPW (SEQ ID NO: 8), IVTHSDPW (SEQ ID NO: 9), VVTHSDPW (SEQ ID NO: 10), TVTHTDPW (SEQ ID NO: 11), TVKHTDPW (SEQ ID NO: 12), TVRHTDPW (SEQ ID NO: 13), TVYHSDPW (SEQ ID NO: 14), and VVVSTDPW (SEQ ID NO: 15).

In the peptide represented by the formula [I], $Xaa_9$-$Xaa_{10}$-$Xaa_{11}$-$Xaa_{12}$-$Xaa_{13}$-$Xaa_{14}$-$Xaa_{15}$ (SEQ ID NO: 229) may be selected from VNGLWLR (SEQ ID NO: 16), VNGLWFP (SEQ ID NO: 17), VNGLWFY (SEQ ID NO: 18), VNGLWLW (SEQ ID NO: 19), VNGLWLQ (SEQ ID NO: 20), ANGLWLA (SEQ ID NO: 21), and VNGLYLD (SEQ ID NO: 22).

The peptide represented by the formula [I] may be selected from the following sequences:
HVTHQDPWVNGLWIA (SEQ ID NO: 23), VVSHHDPWVNGLFIA (SEQ ID NO: 24), VVVHADPWVNGLWIQ (SEQ ID NO: 25), VVKHPDPWVNGLYFH (SEQ ID NO: 26), VVQHRDPWVNGLWFP (SEQ ID NO: 27), SVVHSDPWVNGLYLS (SEQ ID NO: 28), AVKHSDPWVNGLYLP (SEQ ID NO: 29), SVTHIDPWVNGLYLP (SEQ ID NO: 30), KVSHFDPWVNGLWLP (SEQ ID NO: 31), TVTHRDPWVNGLILS (SEQ ID NO: 32), QVSHPDPWVNGLILQ (SEQ ID NO: 33), TVYSDDPWVNGLWLR (SEQ ID NO: 34), SVYGLDPWINGLRFV (SEQ ID NO: 35), TVFHTDPWVNGLWIS (SEQ ID NO: 36), TVRHTDPWVNGLWIS (SEQ ID NO: 37), TVKHPDPWVNGLWIS (SEQ ID NO: 38), TVTHSDPWVNGLFLP (SEQ ID NO: 39), VVTHPDPWVNGLFLP (SEQ ID NO: 40), TVTHIDPWVNGLWLP (SEQ ID NO: 41), TVVHADPWVNGLYLP (SEQ ID NO: 42), TVVHSDPWVNGLWLP (SEQ ID NO: 43), TVIHPDPWVNGLWLP (SEQ ID NO: 44), IVSHPDPWVNGLWLP (SEQ ID NO: 45), SVSHPDPWVNGLWLP (SEQ ID NO: 46), EVSHPDPWVNGLWIP (SEQ ID NO: 47), IVYHADPWVNGLWLS (SEQ ID NO: 48), VVRHSDPWVNGLWID (SEQ ID NO: 49), VVYSSDPWVNGLHLT (SEQ ID NO: 50), TVSHPDPWVNGLWIR (SEQ ID NO: 51), TVYHPDPWVNGLWIR (SEQ ID NO: 52), TVWHPDPWVNGLWIY (SEQ ID NO: 53), EVKHPDPWVNGLWIY (SEQ ID NO: 54), TVVHPDPWVNGLWIS (SEQ ID NO: 55), TVRHPDPWVNGLWLS (SEQ ID NO: 56), TVRHPDPWVNGLWFS (SEQ ID NO: 57), TVSHPDPWVNGLWLQ (SEQ ID NO: 58), TVTHPDPWVNGLWLP (SEQ ID NO: 59), TVTHPDPWVNGLYLP (SEQ ID NO: 60), TVYHPDPWVNGLWLP (SEQ ID NO: 61), TVVHPDPWVNGLWLP (SEQ ID NO: 62), TVFHPDPWVNGLWIP (SEQ ID NO: 63), AVTHSDPWVNGLWLP (SEQ ID NO: 64), TVTHSDPWVNGLWFP (SEQ ID NO: 65), EVSHPDPWVNGLWFP (SEQ ID NO: 66), AVSHPDPWVNGLWFP (SEQ ID NO: 67), and SVVHHDPWVNGLWFP (SEQ ID NO: 68).

In another aspect of the present invention, the peptide contains 15 amino acids represented by the following formula [II]:

[II] (SEQ ID NO: 142)
$Xaa_{16}-Xaa_{17}-Xaa_{18}-Xaa_{19}-Xaa_{20}-Xaa_{21}-Xaa_{22}-Xaa_{23}-$ $Xaa_{24}-Xaa_{25}-Xaa_{26}-Xaa_{27}-Xaa_{28}-Xaa_{29}-Xaa_{30}$ ...

wherein $Xaa_{24}$ represents His or a derivative thereof, $Xaa_{25}$ represents Pro or a derivative thereof, $Xaa_{16}$ to $Xaa_{23}$ and $Xaa_{26}$ to $Xaa_{30}$ each represent an arbitrary amino acid or a derivative thereof.

In the formula [II], $Xaa_{24}$ represents His or a derivative thereof and $Xaa_{25}$ represents Pro or a derivative thereof.

As shown later in Examples, the present inventors have found that a peptide represented by the following formula: MCAB-L-Phe-Ile-Gly-His-Tyr-Arg-Val-Lys-Val-His-Pro-Ile-Ser-Leu-Glu-Arg-Cys (SEQ ID NO: 137) (which will hereinafter be called "BL1") strongly binds to VEGFR2 with high specificity and inhibits the function thereof. As a result of optimization of the sequence from the standpoint of a binding property to VEGFR2, it has been verified that $Xaa_{24}$ and $Xaa_{25}$ each represent the same amino acid in any peptide before and after optimization. These two amino acids, among 15 amino acids, are therefore presumed to be particularly important in binding to VEGFR2.

The other amino acid residues, that is, $Xaa_{15}$ to $Xaa_{23}$ and $Xaa_{29}$ to $Xaa_{30}$ are independently selected from arbitrary amino acids and derivatives thereof.

It is also preferred that $Xaa_{16}$ to $Xaa_{23}$ and $Xaa_{26}$ to $Xaa_{30}$ are selected from compounds having the following characteristics.

$Xaa_{16}$: a hydrophobic amino acid or a derivative thereof, particularly, Val or Ile.

$Xaa_{17}$: an arbitrary amino acid or a derivative thereof, particularly, Gly or Asn.

$Xaa_{18}$: an arbitrary amino acid or a derivative thereof, such as Pro or Gly.

$Xaa_{19}$: an aromatic amino acid or a derivative thereof.

$Xaa_{20}$: an arbitrary amino acid or a derivative thereof such as Arg.

$Xaa_{21}$: a hydrophobic aliphatic amino acid, particularly, Ile or Val.

$Xaa_{22}$: an amino acid having a positive charge such as Lys or Arg.

$Xaa_{23}$: a hydrophobic aliphatic amino acid, particularly, Val.

$Xaa_{26}$: a hydrophobic aliphatic amino acid, particularly, Val or Ile.

$Xaa_{27}$: a hydrophilic amino acid having no charge, particularly, Ser.

$Xaa_{28}$: a hydrophobic amino acid, particularly, Leu.

$Xaa_{29}$: an arbitrary amino acid or a derivative thereof, particularly, Glu.

$Xaa_{30}$: an arbitrary amino acid or a derivative thereof, particularly, Pro or an aromatic amino acid.

The above-described characteristics of the $Xaa_{16}$ to $Xaa_{23}$ and $Xaa_{26}$ to $Xaa_{30}$ are those found both in the sequence of BL1 that binds to VEGFR2 and thereby inhibits the activity thereof and in the optimized sequence thereof so that a peptide having any of the above-described characteristics is presumed to have a very high possibility of having VEGFR2 inhibiting activity similar to BL1.

In the peptide represented by the formula [III], $Xaa_{16}-Xaa_{17}-Xaa_{18}-Xaa_{19}-Xaa_{20}-Xaa_{21}-Xaa_{22}-Xaa_{23}$ (SEQ ID NO: 230) may be selected from the group consisting of VNGYRVKV (SEQ ID NO: 69), VNGYSIKV (SEQ ID NO: 70), INGYKIKV (SEQ ID NO: 71), IGPYKIRV (SEQ ID NO: 72), IGPYRIRL (SEQ ID NO: 73), YGPYAIKV (SEQ ID NO: 74), IGPYVIKV (SEQ ID NO: 75), IGRFRIKV (SEQ ID NO: 76), LGRWSIKV (SEQ ID NO: 77), IGSFVIRV (SEQ ID NO: 78), IRGFRIRV (SEQ ID NO: 79), VGPYRIRV (SEQ ID NO: 80), VGIYQIRV (SEQ ID NO: 81), IGHYRVKV (SEQ ID NO: 82), and IGHYRVKV (SEQ ID NO: 83).

In the peptide represented by the formula [III], $Xaa_{24}-Xaa_{25}-Xaa_{26}-Xaa_{27}-Xaa_{28}-Xaa_{29}-Xaa_{30}$ (SEQ ID NO: 231) may be selected from HPISLAP (SEQ ID NO: 84), HPISLSP (SEQ ID NO: 85), HPISLEP (SEQ ID NO: 86), HPISLEY (SEQ ID NO: 87), HPISLEW (SEQ ID NO: 88), HPISLLP (SEQ ID NO: 89), HPVSLEP (SEQ ID NO: 90), HPVSFEP (SEQ ID NO: 91), HPVSLES (SEQ ID NO: 92), HPVSLEY (SEQ ID NO: 93), HPVTLAW (SEQ ID NO: 94), HPVGLWP (SEQ ID NO: 95), and HPISLER (SEQ ID NO: 96).

The peptide represented by the formula [II] may be selected from the following sequences: LNGYYVKVHPVSLEP (SEQ ID NO: 97), LNGYRVKVHPISLEP (SEQ ID NO: 98), VGPYAVKVHPISLSP (SEQ ID NO: 99), VGHYRVKVHPISLLP (SEQ ID NO: 100), IGAYKVKVHPISLQP (SEQ ID NO: 101), LGPYRVKVHPISLHF (SEQ ID NO: 102), IGPYLVKVHPVSLHF (SEQ ID NO: 103), IGEYRVKVHPISLAP (SEQ ID NO: 104), IGPYRVKVHPVSLLP (SEQ ID NO: 105), IGIYRVKVHPVSLEP (SEQ ID NO: 106), IGPYAVKVHPVSLEP (SEQ ID NO: 107), IGTWVVKVHPVSLEP (SEQ ID NO: 108), INSYVVKVHPISLEP (SEQ ID NO: 109), ILGYFVKVHPVSLDP (SEQ ID NO: 110), YNGFAVKVHPISLEN (SEQ ID NO: 111), VNGYAVKVHPVSLEP (SEQ ID NO: 112), VNGYIVKVHPVSLEP (SEQ ID NO: 113), IYGFAVKVHPVSLEP (SEQ ID NO: 114), IGIYRVKVHPISLEY (SEQ ID NO: 115), IGIFRVKVHPISLEP (SEQ ID NO: 116), IGIYRVKVHPISLEP (SEQ ID NO: 117), IGRYAVKVHPISLEP (SEQ ID NO: 118), IGPYWVKVHPISLLP (SEQ ID NO: 119), IGPYHVKVHPVSLEP (SEQ ID NO: 120), IGPWFVKVHPVSLEP (SEQ ID NO: 121), IGPYRVKVH-PVSLEY (SEQ ID NO: 122), IGPYRVKVHPISLEW (SEQ ID NO: 123), VNGYRVKVHPISLDW (SEQ ID NO: 124), LYGYRVKVHPISLEP (SEQ ID NO: 125), IGIYRVKVH-PISLEP (SEQ ID NO: 126), IGPYRVKVHPISLEP (SEQ ID NO: 127), IGPYWVKVHPISLEP (SEQ ID NO: 128), IGPYRVKVHPVSLEP (SEQ ID NO: 129), IGPYRIKVH-PVSLEP (SEQ ID NO: 130), VGPYRVKVHPVSLEP (SEQ ID NO: 131), IGPYVVKVHPVSLEP (SEQ ID NO: 132), IGPYRVKVHPVSLEY (SEQ ID NO: 133), IGPYWVK-VHPVSLEW (SEQ ID NO: 134), and INGYYVKVH-PVSLDW (SEQ ID NO: 135).

The term "hydrophilic amino acid" as used herein means Asp, Glu, Arg, Lys, His, Gly, Ser, Thr, Cys, Asn, Gin, or Tyr, or a hydrophilic derivative thereof. The term "hydrophobic amino acid" as used herein means Ala, Val, Leu, lie, Met, Tyr, Trp, Phe, or Pro, or a hydrophobic derivative thereof. The term "hydrophobic aliphatic amino acid" means Ala, Leu, Val, or lie, or a hydrophobic derivative thereof; the term "aromatic amino acid" means Tyr, Trp, or Phe or a derivative thereof; the term "amino acid having a positive charge" means Lys, Arg, or His, or a derivative thereof having a positive charge; the term "hydrophilic amino acid having no charge" means Gly, Ser, Thr, Cys, Asn, or Gin or a hydrophilic derivative thereof having no charge.

The peptide according to the present invention embraces a peptide obtained by deleting, adding, or substituting one or several amino acids in the amino acid sequence represented by the formula [I] or [II] and having inhibiting activity against a vascular endothelial growth factor receptor VEGFR2.

When the term "peptide obtained by deleting, adding, or substituting one or several amino acids" is used herein, the number of amino acids to be deleted or the like is not particularly limited insofar as the resulting peptide has VEGFR2 inhibiting activity. Examples of the number include one, two, three, four, and five. The deletion, addition, or substitution may occur either at the end or in the middle of the peptide and further, it may occur either at one place or at two or more places.

The term "having VEGFR2 inhibiting activity" as used herein means having activity inhibiting the activity of VEGFR2 in vitro and/or in vivo and presence of such inhibiting activity can be verified in a known manner by those skilled in the art. Examples of a method of verifying the inhibiting activity include, but not limited to, a method of incubating, in the presence of VEGF, HUVEC (Human Umbilical Vein Endothelial Cells) that express VEGFR2 and a peptide and determining the presence or absence of phosphorylation of VEGFR2 by dot blotting assay; a method of administering a peptide to HUVEC cells that express VEGFR2 and determining the presence or absence of growth or a growth rate; a method of coculturing HUVEC and a fibroblast in the presence of VEGF, administering a peptide, and determining the presence or absence of angiogenesis; and a method of administering a peptide to model animals such as cancer-carrying mice and determining the presence or absence of angiogenesis.

The term "having VEGFR2 inhibiting activity" as used herein means, in vitro or in vivo, suppressing phosphorylation of VEGFR2, suppressing or retarding the growth of HUVEC cells, suppressing or retarding angiogenesis, or the like and when a peptide exhibits any one of these effects, it is regarded to have VEGFR2 inhibiting activity.

The peptide of the present invention has, at the C terminal thereof, not only a carboxyl group or a carboxylate group but also an amide or ester. The polypeptide of the present invention includes salts of a polypeptide. As the salts of a polypeptide, salts of a physiologically acceptable base or acid may be used. Examples include inorganic acid (hydrochloric acid, hydrobromic acid, hydroiodic acid, sulfuric acid, phosphoric acid, or the like) addition salts, organic acid (p-toluenesulfonic acid, methanesulfonic acid, oxalic acid, p-bromophenylsulfonic acid, carboxylic acid, succinic acid, citric acid, benzoic acid, acetic acid, or the like) addition salts, inorganic bases (ammonium hydroxide, alkali or alkaline earth metal hydroxides, carbonates, and bicarbonates, or the like), and amino acid addition salts.

The peptide of the present invention may be modified, for example, phosphorylated, methylated, acetylated, adenylated, ADP ribosylated, glycosylated, or the like insofar as the modified one can overcome the problem of the present invention. The peptide of the present invention may be fused with another peptide or protein.

The peptide of the present invention can be prepared by a known peptide synthesis process, for example, chemical synthesis processes such as liquid phase synthesis, solid phase synthesis, and hybrid synthesis using liquid phase synthesis and solid phase synthesis in combination, genetic recombination, cell-free translation synthesis.

In solid phase synthesis, for example, esterification is performed between the hydroxyl group of a hydroxyl-containing resin and the carboxyl group of a first amino acid (usually, the C-terminal amino acid of an intended peptide) having an α-amino group protected with a protecting group. As an esterifying catalyst, usable is a known dehydration condensation agent such as 1-mesitylenesulfonyl-3-nitro-1, 2,4-triazole (MSNT), dicyclohexylcarbodiimide (DCC), or diisopropylcarbodiimide (DIPCDI).

Next, the protecting group is removed from the α-amino group of the first amino acid and at the same time, a second amino acid having functional groups, other than the carboxyl group of the main chain, all protected is added to activate the carboxyl group and bind the second amino acid to the first amino acid. Then, the α-amino group of the second amino acid is deprotected and a third amino acid having functional groups, other than the carboxyl group of the main chain, all protected is added to activate the carboxyl group and bind the third amino acid to the second amino acid. After a peptide having a desired length is synthesized by repeating the above-mentioned steps, all the functional groups are deprotected.

Examples of the resin to be used in solid-phase synthesis include Merrifield resin, MBHA resin, CI-Trt resin, SASRIN resin, Wang resin, Rink amide resin, HMFS resin, Amino-PEGA resin (Merck), and HMPA-PEGA resin (Merck). These resins may be provided for use after washing with a solvent (such as dimethylformamide (DMF), 2-propanol, or methylene chloride).

Examples of the protecting group of the α-amino group include a benzyloxycarbonyl (Cbz or Z) group, a tert-butoxycarbonyl (Boc) group, fluorenylmethoxycarbonyl (Fmoc) group, a benzyl group, an allyl group, and an allyloxycarbonyl (Alloc) group. The Cbz group can be removed using hydrofluoric acid, hydrogenation, or the like; the Boc group can be removed using trifluoroacetic acid (TFA); and the Fmoc group can be removed by the treatment with piperidine.

The α-carboxyl group can be protected with a methyl ester, an ethyl ester, a benzyl ester, a tert-butyl ester, a cyclohexyl ester, or the like.

As other functional groups of amino acids, the hydroxyl group of serine or threonine can be protected with a benzyl group or tert-butyl group; and the hydroxyl group of tyrosine can be protected with a 2-bromobenzyloxycarbonyl group or tert-butyl group. The amino group of the lysine side chain or the carboxyl group of glutamic acid or aspartic acid can be protected in a manner similar to that used for protecting the α-amino group or α-carboxyl group.

The carboxyl group can be activated using a condensing agent. Examples of the condensing agent include dicyclohexylcarbodiimide (DCC), diisopropylcarbodiimide (DIPCDI), 1-ethyl-3-(3-dimethylaminopropyl)carbodiimide (EDC or WSC), (1H-benzotriazol-1-yloxy)tris(dimethylamino)phosphonium hexafluorophosphate (BOP), 1-[bis(dimethylamino)methyl]-1H-benzotriazolium-3-oxide hexafluorophosphate (HBTU).

A peptide chain can be cleaved from the resin by treating it with an acid such as TFA or hydrogen fluoride (HF).

Preparation of a peptide by genetic recombination or cell-free translation system can be performed using a nucleic acid (DNA or RNA) encoding the peptide of the present invention.

The nucleic acid encoding the peptide of the present invention can be prepared by a known process or a process equivalent thereto. For example, it can be synthesized by an automatic synthesizer. A restriction site may be added in order to insert the resulting DNA into a vector, or a base sequence encoding an amino acid sequence for cleaving the resulting peptide chain by an enzyme may be incorporated.

The nucleic acid encoding the peptide of the present invention can be expressed by inserting it downstream of a promoter of an expression vector. Examples of the vector usable here include *Escherichia coli*-derived plasmids (such as pBR322, pBR325, pUC12, pUC13, pUC18, pUC19, pUC118, and pBluescript II), *Bacillus subtilis*-derived plasmids (such as pUB110, pTP5, pC1912, pTP4, pE194, and pC194), yeast-derived plasmids (such as pSH19, pSH15, YEp, YRp, YIp, and YAC), bacteriophages (such as λ phage and M13 phage), viruses (retrovirus, vaccinia virus, adenovirus, adeno-associated virus (AAV), cauliflower mosaic virus, tobacco mosaic virus, and baculovirus), and cosmids.

The promoter can be selected as needed in accordance with the kind of a host. When the host is an animal cell, for example, SV40 (simian virus 40)-derived promoter or CMV (cytomegalovirus)-derived promoter can be used. When the host is *Escherichia coli*, a trp promoter, a T7 promoter, lac promoter, or the like can be used.

The expression vector may contain a DNA replication origin (ori), a selection marker (antibiotic resistance, nutrition requirements, or the like), an enhancer, a splicing signal, a poly-A additional signal, a nucleic acid encoding a tag (FLAG, HA, GST, GFP, or the like), and the like.

The expression vector containing the nucleic acid encoding the peptide of the present invention may be used for transforming a host in vitro as described below and thereby expressing the peptide of the present invention or may be used for administering it to an object as is and thereby expressing the peptide of the present invention in vivo.

The host to be used for transformation can be selected as needed based on the relation with the vector and for example, *Escherichia coli*, *Bacillus subtilis*, *Bacillus* bacteria), yeasts, insects or insect cells, and animal cells can be used. Examples of the animal cells include HEK293T cells, CHO cells, COS cells, myeloma cells, HeLa cells, and Vero cells. Transformation can be performed in a known manner such as lipofection, calcium phosphate method, electroporation, microinjection, or particle gun technology, depending on the kind of the host.

The transformant is then cultured by a conventional method to express an intended peptide. A medium is selected as needed in accordance with the kind of the host.

Purification of the peptide from the culture of the transformant can be performed in the following manner. After cultured cells are collected and then suspended in an appropriate buffer, the resulting suspension is subjected to ultrasonic treatment, freezing and thawing, or the like to destruct the cells. Then centrifugation or filtration is performed to obtain a crude product. When the peptide is secreted in the culture medium, the supernatant is collected.

Purification of the crude extract or culture supernatant can also be performed by a known method or a method equivalent thereto (for example, salting-out, dialysis, ultrafiltration, gel filtration, SDS-PAGE, ion exchange chromatography, affinity chromatography, or reverse-phase high-performance liquid chromatography).

The peptide thus obtained may be converted from a free form to a salt or from a salt to a free form by a known method or a method equivalent thereto.

The translation synthesis system may be a cell-free translation system. The cell-free translation system is called "cell-free protein synthesis system" and it is a system not using cells such as *Escherichia coli* as are but using an intracellular component in *Escherichia coli* or the like. This system includes a system mainly using a cell extract and a system using a reaction liquid (reconstituted cell-free translation system) reconstituted of purified components of the cell extract. By the cell-free translation system, a high-purity peptide can be obtained without purifying the expression product.

Examples of the system mainly using a cell extract include systems using an *Escherichia coli* extract, a wheat germ extract, a rabbit reticulocyte extract, and an insect cell extract.

The reconstituted cell-free translation system can be constructed of a ribosomal protein, aminoacyl tRNA synthetase (ARS), ribosomal RNA, amino acid, rRNA, GTP, ATP, translation initiation factor (IF), elongation factor (EF), termination factor (RF), ribosome regeneration factor, another factor necessary for translation, and the like, each of which has been purified.

Energy may be supplied continuously to the system containing them by dialysis. The system may contain RNA polymerase for carrying out transcription from DNA at the same time. Examples of a commercially available cell-free translation system usable here include an *Escherichia coli*-derived system such as RTS-100" (registered trade mark) of Roche Diagnostics Corp. and PURESYSTEM (registered trade mark) of PGI Corporation and a system using a wheat germ extract available from ZOEGENE Corporation and Cell-free Science.

When the cell-free translation system is used, a high-purity peptide can be obtained without purifying the expression product.

In the cell-free translation system, an artificial aminoacyl tRNA obtained by linking (acylating) a desired amino acid, hydroxy acid, or carboxylic acid to a tRNA having an arbitrary anticodon may be used instead of an aminoacyl tRNA synthesized with a natural aminoacyl tRNA synthetase. Such an aminoacyl tRNA can be synthesized using an artificial ribozyme.

Examples of such a ribozyme include flexizyme (H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006)

Nature Methods 3, 357-359 "The flexizyme system: a highly flexible tRNA aminoacylation tool for the synthesis of nonnatural peptides"; N. Niwa, Y. Yamagishi, H. Murakami, H. Suga (2009) Bioorganic & Medicinal Chemistry Letters 19, 3892-3894 "A flexizyme that selectively charges amino acids activated by a water-friendly leaving group"; WO2007/066627; and the like). Flexizyme is also known under the name of flexizyme (Fx) in original form and also under the name of a modified one such as dinitrobenzyl flexizyme (dFx), enhanced flexizyme (eFx), or aminoflexizyme (aFx).

Flexizyme enables binding of a desired amino acid, hydroxy acid, or carboxylic acid to a tRNA having an arbitrary codon, which makes it possible to translate while associating a desired codon with the desired amino acid, hydroxy acid, or carboxylic acid. As the desired amino acid, a special amino acid may be used.

Examples of the special amino acid are shown in the following table, but it is not limited to them. In the table, DBE and CME are esters to be used when the special amino acid is bound to tRNA by using flexizyme. DBE represents a 3,5-dinitrobenzyl ester and CME represents a cyanomethyl ester.

TABLE 1

Initiator amino acids

| | |
|---|---|
| Acetyl-L-alanine | DBE |
| Acetyl-L-phenylalanine | CME |
| Acetyl-L-tyrosine | CME |
| Acetyl-L-tryptophan | CME |
| Acetyl-D-alanine | DBE |
| Acetyl-D-phenylalanine | CME |
| Acetyl-D-tyrosine | CME |
| Acetyl-D-tryptophan | CME |
| N-Chloroacetyl-L-alanine | DBE |
| N-Chloroacetyl-L-phenylalanine | CME |
| N-Chloroacetyl-L-tyrosine | CME |
| N-Chloroacetyl-L-tryptophan | CME |
| N-Chloroacetyl-D-alanine | DBE |
| N-Chloroacetyl-D-phenylalanine | CME |
| N-Chloroacetyl-D-tyrosine | CME |
| N-Chloroacetyl-D-tryptophan | CME |
| N-3-chloromethylbenzoyl-L-tyrosine | CME |
| N-3-chloromethylbenzoyl-L-tryptophane | CME |

TABLE 2

Amino acids that crosslink in peptide

| | |
|---|---|
| Nγ-(2-chloroacetyl)-α,γ-diaminobutylic acid | DBE |
| Nγ-(2-chloroacetyl)-α,γ-diaminopropanoic acid | DBE |

TABLE 3

D-amino acids

| | |
|---|---|
| D-Serine | DBE |
| D-Phenylalanine | CME |
| D-Tyrosine | CME |
| D-Tryptophan | CME |

TABLE 4

N-methylamino acids

| | |
|---|---|
| N-methyl-Glycine | DBE |
| N-methyl-Alanine | DBE |

TABLE 4-continued

N-methylamino acids

| | |
|---|---|
| N-methyl-Serine | DBE |
| N-methyl-Histidine | DBE |
| N-methyl-Phenylalanine | CME |
| N-methyl-Tyrosine | CME |
| N-methyl-Tryptophan | CME |

TABLE 5

Peptoid block

| | |
|---|---|
| N-ethyl-Glycine | DBE |
| N-n-propyl-Glycine | DBE |
| N-n-butyl-Glycine | DBE |
| N-n-pentyl-Glycine | DBE |
| N-n-hexyl-Glycine | DBE |
| N-n-heptyl-Glycine | DBE |
| N-n-octyl-Glycine | DBE |
| N-isopentyl-Glycine | DBE |
| N-(2-phenylethyl)-Glycine | CME |
| N-(3-phenylpropyl)-Glycine | CME |
| N-[2-(p-hydroxyphenyl)ethyl]-Glycine | CME |

TABLE 6

Other special amino acids

| | |
|---|---|
| p-biphenylalanine | CME |
| p-trifluoromethylphenylalanine | CME |
| p-azidophenylalanine | CME |
| p-biotinyl-aminophenylalanine | CME |
| e-N-Biotinyl-lysine | DBE |
| e-N-Acetyl-lysine | DBE |
| L-Citrulline | DBE |
| L-5-Hydroxytryptphan | CME |
| L-1,2,3,4,-Tetrahydroisoquinoline-3-carboxylic acid | DBE |
| Aminoisobutyric acid | DBE |
| N-methyl-aminoisobutyric acid | DBE |
| N-methyl-Phenylglycine | CME |

In one aspect, the peptide of the present invention may be cyclized and a cyclized peptide is also embraced in the peptide of the present invention. The term "cyclize" as used herein means that within one peptide, two amino acids separated from each other with one or more amino acids therebetween are bound to each other directly or indirectly via a linker or the like and thereby form a cyclic structure in the molecule.

The peptide can be cyclized via disulfide bonds, peptide bonds, alkyl bonds, alkenyl bonds, ester bonds, thioester bonds, ether bonds, thioether bonds, phosphonate ether bonds, azo bonds, C—S—C bonds, C—N—C bonds, C=N—C bonds, amide bonds, lactam bridges, carbamoyl bonds, urea bonds, thiourea bonds, amine bonds, thioamide bonds, or the like, but bonds are not limited to them.

The peptide may have a stable structure and have enhanced affinity to a target by cyclization.

For cyclization of the peptide, when it contains, for example, an amino acid having a functional group 1 shown below and an amino acid having a functional group 2 corresponding thereto, a translationally synthesized peptide can be macrocyclized by a spontaneous reaction. The peptide may have, at an N-terminal side thereof, either the functional group 1 or the functional group 2. It may have them at the N terminal and the C terminal thereof, respectively. It may have one of the functional groups as one terminal amino acid and the other group as a non-terminal amino acid or it may have both of these functional groups as a non-terminal amino acid.

TABLE 7

| Functional group 1 | Functional group 2 |
|---|---|
| (A) —C(=O)—CH$_2$—X$_1$ (A-1) | HS— (A-2) |
| (B) —C≡C—H (B-1) | N$_3$— (B-2) |
| (C) —Ar—CH$_2$NH$_2$ (C-1) | 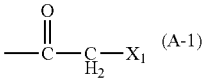 (C-2) |
| (D) —C≡C—CH$_2$—X$_1$ (D-1) | HS— (D-2) |
| (E) —Ar—CH$_2$—X$_1$ (E-1) | HS— (E-2) |

In the formula, $X_1$ represents Cl, Br, or I and Ar represents an aromatic ring which may have substituent(s).

As the amino acid having a functional group (A-1), a chloroacetylated amino acid can be used. Examples of the chloroacetylated amino acid include N-chloroacetyl-L-alanine, N-chloroacetyl-L-phenylalanine, N-chloroacetyl-L-tyrosine, N-chloroacetyl-L-tryptophan, N-3-(2-chloroacetamido)benzoyl-L-phenylalanine, N-3-(2-chloroacetamido)benzoyl-L-tyrosine, N-3-(2-chloroacetamido)benzoyl-L-tryptophane, β-N-chloroacetyl-L-diaminopropanoic acid, γ-N-chloroacetyl-L-diaminobutyric acid, σ-N-chloroacetyl-L-ornithine, and ε-N-chloroacetyl-L-lysine, and D-amino acid derivatives corresponding thereto.

Examples of the amino acid having a functional group (A-2) include cysteine, homocysteine, mercaptonorvaline, mercaptonorleucine, 2-amino-7-mercaptoheptanoic acid, and 2-amino-8-mercaptooctanoic acid, and amino acids obtained by protecting the SH group of the above-mentioned amino acids and then removing the protecting group, and D-amino acid derivatives corresponding thereto.

Cyclization may be performed according to the method described in, for example, Kawakami, T. et al., Nature Chemical Biology 5, 888-890 (2009); Yamagishi, Y. et al., ChemBioChem 10, 1469-1472 (2009); Sako, Y. et al., Journal of American Chemical Society 130, 7932-7934 (2008); Goto, Y. et al., ACS Chemical Biology 3, 120-129 (2008); Kawakami T. et al, Chemistry & Biology 15, 32-42 (2008); and WO2008/117833.

As the amino acid having a functional group (B-1), for example, propargylglycine, homopropargylglycine, 2-amino-6-heptynoic acid, 2-amino-7-octynoic acid, and 2-amino-8-nonynoic acid can be used. In addition, 4-pentynoylated or 5-hexynoylated amino acids can also be used. Examples of the 4-pentynoylated amino acids include N-(4-pentenoyl)-L-alanine, N-(4-pentenoyl)-L-phenylalanine, N-(4-pentenoyl)-L-tyrosine, N-(4-pentenoyl)-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophane, β-N-(4-pentenoyl)-L-diaminopropanoic acid, γ-N-(4-pentenoyl)-L-diaminobutyric acid, σ-N-(4-pentenoyl)-L-ornithine, and ε-N-(4-pentenoyl)-L-lysine, and D-amino acid derivatives corresponding thereto.

As the amino acid having a functional group (B-2), for example, azidoalanine, 2-amino-4-azidobutanoic acid, azidoptonorvaline, azidonorleucine, 2-amino-7-azidoheptanoic acid, and 2-amino-8-azidooctanoic acid can be used. In addition, azidoacetylated or 3-azidopentanoylated amino acids can also be used. Examples of the azidoacetylated amino acids include N-azidoacetyl-L-alanine, N-azidoacetyl-L-phenylalanine, N-azidoacetyl-L-tyrosine, N-azidoacetyl-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophane, β-N-azidoacetyl-L-diaminopropanoic acid, γ-N-azidoacetyl-L-diaminobutyric acid, σ-N-azidoacetyl-L-ornithine, and ε-N-azidoacetyl-L-lysine, and D-amino acid derivatives corresponding thereto.

The circularization can be performed according to the method described in, for example, Sako, Y. et al., Journal of American Chemical Society 130, 7932-7934 (2008) or WO2008/117833.

Examples of the amino acid having a functional group (C-1) include N-(4-aminomethyl-benzoyl)-phenylalanine ($_{AMB}$F) and 4-3-aminomethyltyrosine.

Examples of the amino acid having a functional group (C-2) include 5-hydroxytryptophan (W$_{OH}$).

The circularization can be performed according to the method described in, for example, Yamagishi, Y. et al., ChemBioChem 10, 1469-1472 (2009) or WO2008/117833.

Examples of the amino acid having a functional group (D-1) include 2-amino-6-chloro-hexynoic acid, 2-amino-7-chloro-heptynoic acid, and 2-amino-8-chloro-octynoic acid.

Examples of the amino acid having a functional group (D-2) include cysteine, homocysteine, mercaptonorvaline, mercaptonorleucine, 2-amino-7-mercaptoheptanoic acid, and 2-amino-8-mercaptooctanoic acid, amino acids obtained by protecting the SH group of these amino acids and then removing the protecting group, and D-amino acid derivatives corresponding thereto.

The circularization can be performed according to the method described in, for example, WO2012/074129.

Examples of the amino acid (E-1) include N-3-chloromethylbenzoyl-L-phenylalanine, N-3-chloromethylbenzoyl-L-tyrosine, and N-3-chloromethylbenzoyl-L-tryptophane.

Examples of the amino acid (E-2) include cysteine, homocysteine, mercaptonorvaline, mercaptonorleucine, 2-amino-7-mercaptoheptanoic acid, and 2-amino-8-mercaptooctanoic acid, amino acids obtained by protecting the SH group of these amino acids and then removing the protecting group, and D-amino acid derivatives corresponding thereto.

The pharmaceutical composition of the present invention contains the above-mentioned peptide as an active ingredient and is capable of suppressing angiogenesis in malignant tumors or retinopathy through the peptide which binds to VEGFR2 and thereby inhibits the activity thereof.

The administration route of the pharmaceutical composition is not particularly limited and it can be administered either orally or parenterally. Examples of the parenteral administration include administration by injection such as intramuscular, intravenous, or subcutaneous injection, transdermal administration, and transmucosal administration (nasal, buccal, ocular, pulmonary, vaginal, or rectal).

Since the peptide in the pharmaceutical composition is likely to be metabolized and excreted, it can be subjected to various modifications. For example, a polypeptide can have longer residence time in blood and reduced antigenicity by adding thereto polyethylene glycol (PEG) or sugar chain. A polypeptide may be encapsulated in an emulsion, nanoparticles, nanospheres, or the like used as a sustained-release base and prepared using a biodegradable polymer compound such as polylactic acid-glycol (PLGA), porous hydroxyapatite, liposome, surface-modified liposome, or unsaturated fatty acid. When it is administered transdermally, it can be penetrated through the stratum corneum by passing a weak electrical current through the skin surface (iontophoresis)

With regard to the pharmaceutical composition, the active ingredient thereof may be used as is or a preparation obtained by adding thereto a pharmaceutically acceptable carrier, excipient, additive, or the like may be used. Examples of the preparation include liquids and solutions (for example, injections), dispersions, suspensions, tablets, pills, powders, suppositories, powdered drug, fine granules, granules, capsules, syrups, lozenges, inhalants, ointments, ophthalmic preparations, nasal preparations, ear preparations, and cataplasms.

The preparation can be obtained in a conventional manner by using, for example, an excipient, a binder, a disintegrant, a lubricant, a dissolving agent, a solubilizing agent, a colorant, a taste/odor corrigent, a stabilizer, an emulsifier, an absorption promoter, a surfactant, a pH adjuster, an antiseptic, or an antioxidant as needed.

Examples of the ingredient to be used for obtaining the preparation include, but not limited to, purified water, saline, phosphate buffer, dextrose, glycerol, pharmaceutically acceptable organic solvents such as ethanol, animal or vegetable oils, lactose, mannitol, glucose, sorbitol, crystalline cellulose, hydroxypropyl cellulose, starch, corn starch, silicic anhydride, magnesium aluminum silicate, collagen, polyvinyl alcohol, polyvinylpyrrolidone, carboxyvinyl polymer, carboxymethylcellulose sodium, sodium polyacrylate, sodium alginate, water-soluble dextran, carboxymethyl starch sodium, pectin, methyl cellulose, ethyl cellulose, xanthan gum, gum arabic, tragacanth, casein, agar, polyethylene glycol, diglycerin, glycerin, propylene glycol, petrolatum, paraffin, octyl dodecyl myristate, isopropyl myristate, higher alcohol, stearyl alcohol, stearic acid, and human serum albumin.

Usable examples of the absorption promoter for improving absorption of a poorly absorbable drug having difficulty in transmucosal absorption of the peptide include surfactants such as polyoxyethylene lauryl ethers, sodium lauryl sulfate, and saponin; bile salts such as glycocholic acid, deoxycholic acid, and taurocholic acid; chelating agents such as EDTA and salicylic acid; fatty acids such as caproic acid, capric acid, lauric acid, oleic acid, linoleic acid, and mixed micelle; enamine derivatives, N-acylcollagen peptide, N-acylamino acid, cyclodextrins, chitosans, and nitric oxide donors.

Pills or tablets may be sugar, gastric, or enteric coated.

Injections may contain distilled water for injection, physiological saline, propylene glycol, polyethylene glycol, a vegetable oil, an alcohol, or the like. It may further contain a humectant, an emulsifier, a dispersant, a stabilizer, a dissolving agent, a solubilizing agent, an antiseptic, or the like.

The pharmaceutical composition of the present invention is effective, through inhibiting the function of VEGFR2, for the treatment or prevention of various diseases in which pathological angiogenesis is presumed to be involved. Examples of the diseases in which pathological angiogenesis is involved include, but not limited to, malignant tumor (head and neck cancer, neck cancer, esophageal cancer, gastric cancer, kidney cancer, renal cell cancer, liver cancer, pancreas cancer, gallbladder cancer, breast cancer, lung cancer, non-small-cell lung cancer, colon cancer, large bowel cancers (including colorectal cancer), skin cancer, ovary cancer, bladder cancer, fibrosarcoma, squamous cell carcinoma, neuroectoderm, thyroid tumor, prostatic cancer, lymphoma, hepatocarcinoma, mesothelioma, epidermoid carcinoma, nervous system neoplasms (astrocytoma, oligodendroglioma, meningioma, neurofibroma, glioblastoma, ependymoma, neurilemmoma, neurofibrosarcoma, neuroblastoma, pituitary tumor (for example, hypophyseal adenoma), medulloblastoma, melanoma, and brain tumor), osteosarcoma, Kaposi's sarcoma, hematopoietic tumor of lymphatic system (including leukemia, acute lymphocytic leukemia, acute lymphoblastic leukemia, B cell lymphoma, T cell lymphoma, Hodgkin's lymphoma, non-Hodgkin's lymphoma, hairy cell leukemia, and Burkitt's lymphoma), hematopoietic tumors of myeloid system (including acute and chronic myelocytic leukemia, myelodysplastic syndrome, and promyelocytic leukemia), and tumors derived from mesenchyme (including fibrosarcoma and rhabdomyosarcoma and sarcoma of another site, for example, soft tissue and bone)), benign tumors (for example, thyroid benign tumor and benign prostatic hypertrophy), diabetic retinopathy, rheumatoid arthritis, and arteriosclerosis.

The pharmaceutical composition of the present invention may be used in combination with another drug or therapy useful for the above-mentioned diseases. For example, for malignant tumors, it may be used in combination with various chemotherapies, surgical therapies, or radiation therapies. A drug inhibiting an interaction between VEGF and VEGFR2 and signaling based thereon through a mechanism different from that of the peptide of the present invention may be administered in combination. Specific examples include tyrosine kinase inhibitor of VEGFR2 and a VEGFR2 downstream signaling inhibitor.

The dose of the pharmaceutical composition of the present invention when administered to mammals (for example, humans, mice, rats, guinea pigs, rabbits, dogs, horses, monkeys, and pigs), particularly, humans differs depending on the symptom, age, sex, and weight of patients, difference in sensitivity, administration method, dosing interval, kind of active ingredient, and kind of preparation and is not particularly limited. For example, 30 μg to 1000 mg, 100 μg to 500 mg, or 100 μg to 100 mg of the pharmaceutical composition may be administered once or in several portions. When it is administered by injection, 1 μg/kg to 3000 μg/kg or 3 μg/kg to 1000 μg/kg of it may be administered once or in several portions according to the weight of a patient. As shown in Examples, the peptide of the present invention binds to mouse VEGFR2 so that it is useful as an animal drug or test drug.

Disclosure of all the patent documents and non-patent document cited herein is incorporated herein by reference in its entirety.

EXAMPLE

The present invention will hereinafter be described specifically based on Example. It should however be borne in mind that the present invention is not limited to or by it. Those skilled in the art can change the present invention into various aspects without departing from the meaning of the present invention and such changes are also included in the scope of the present invention.

[1] Selection of a Cyclic Peptide Binding to VEGFR2 by TRAP Display Method

In order to select a cyclic peptide binding to VEGFR2, selection by TRAP display method shown in FIG. 1A was designed. TRAP display method will hereinafter be described briefly but it may be performed based on T. Ishizawa, T. Kawakami, P. C. Reid, H. Murakami (2013) J. Am. Chem. Soc. 135, 5433-5440. First, constructed was a DNA library having a $(NNK)_{8-15}$ sequence encoding a peptide library having, between an initiator amino acid and a Cys residue at the C terminal thereof, from 8 to 15 amino acids at random.

An mRNA library obtained by transcription of the DNA library was translated into a peptide library. The peptide library thus obtained by translation is displayed on its encoding mRNA via a puromycin linker.

Figure 1B:
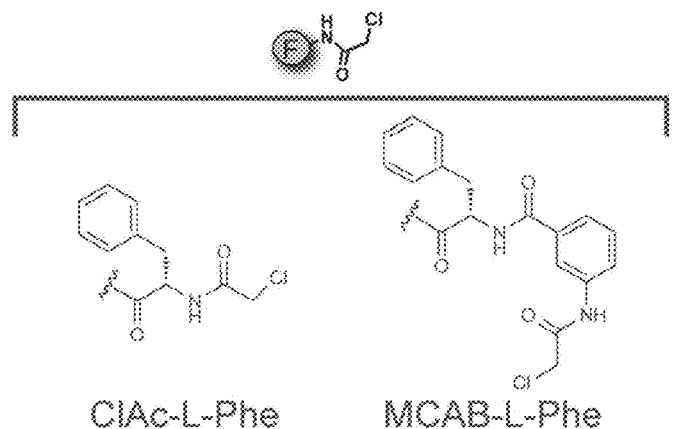
FIG. 1B shows two phenylalanine analogues (ClAc-L-Phe and MCAB-L-Phe) placed at the N terminal for cyclization of a peptide.

Two peptide libraries were constructed by using upon translation, as an initiator amino acid, two phenylalanine analogues (ClAc-L-Phe and MCAB-L-Phe. See FIG. 1B) modified with chloroacetamide by respectively different methods. The respective libraries were prepared using 19 proteinogenic amino acids except Met and an initiator tRNA (prepared using flexizyme based on H. Murakami, A. Ohta, H. Ashigai, H. Suga (2006) Nature Methods 3, 357-359) having either one of the above-mentioned phenylalanine analogues. In the translated libraries, each peptide is cyclized by a reaction between a chloroacetyl group and a Cys residue.

After reverse transcription, peptides binding to the extracellular domain of VEGFR2 immobilized onto magnetic beads were selected and the DNA of the resulting DNA-cyclic peptide complex was amplified by PCR. A peptide library was constructed again using the resulting DNA and a similar operation was performed. A series of operation thus performed was designated as one round and eight rounds of operation were performed. The cDNA amount recovered in each round of selection was determined by real-time PCR. After sixth round, a selection operation was performed at an increased selection pressure.

Figure 2:
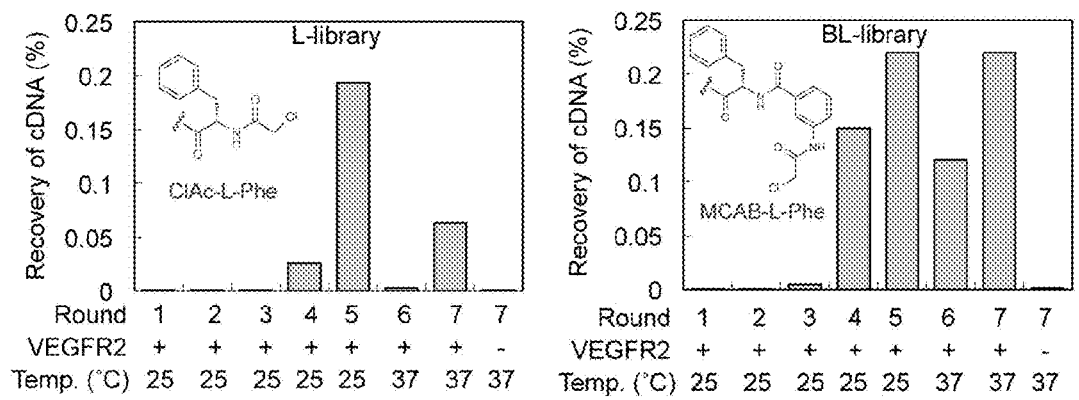
FIG. 2 is a percent recovery of cDNA after each round in the selection of a VEGFR2-binding cyclic peptide in TRAP display method.

A peptide binding to VEGFR2 was obtained from the respective libraries after seventh round of selection operation (FIG. 2).

The following is a sequence of a peptide selected from the library using ClAc-L-Phe as an initiator amino acid. The peptide will hereinafter be called "L1".

```
                                        (SEQ ID NO: 136)
ClAc-L-Phe-Val-Val-Val-Ser-Thr-Asp-Pro-Trp-

Val-Asn-Gly-Leu-Tyr-Ile-Asp-Cys
```

The following is a sequence of a peptide selected from the library using MCAB-L-Phe as an initiator amino acid. The peptide will hereinafter be called "BL1".

```
                                        (SEQ ID NO: 137)
MCAB-L-Phe-Ile-Gly-His-Tyr-Arg-Val-Lys-Val-

His-Pro-Ile-Ser-Leu-Glu-Arg-Cys
```

[2] Binding ability of L1 and BL1 to VEGFR2

Next, L1 and BL1 having, at the C terminal thereof, amidated glycine was synthesized by solid-phase synthesis using a standard Fmoc group.

(1) Synthesis of ClAc-Phe-Val-Val-Val-Ser-Thr-Asp-Pro-Trp-Val-Asn-Gly-Leu-Tyr-Ile-Asp-Cys-Gly (SEQ ID NO: 138)

Solid-phase synthesis was performed through Fmoc/HBTU/HOBt method by placing 0.05 mmol of commercially available Rink Amide-ChemMatrix resin (0.60 mmol/g) in the reactor of a peptide synthesizer Discovery. As a side-chain protecting group of Fmoc amino acid, a $Bu^t$ group was used for Ser, Thr, Asp, and Tyr, a Boc group was used for Trp and Lys, and a Trt group was used for Asn and Cys. The Phe-Val-Val-Val-Ser-Thr-Asp-Pro-Trp-Val-Asn-Gly-Leu-Tyr-Ile-Asp-Cys-Gly-resin (SEQ ID NO: 232) (0.025 mmol) thus obtained was treated with 9.5 mg (0.1 mmol) of 2-chloroacetic acid, 37.9 mg (0.1 mmol) of HBTU, 13.5 mg (0.1 mmol) of HOBt, and 17.0 μl (0.2 mmol) of DIEA to introduce a ClAc group.

After the whole portion (0.025 mmol) of the resin was stirred at room temperature for one hour in 1 ml of a mixture (92.5:2.5:2.5:2.5) of TFA, water, triisopropylsilane, and 3,6-dioxa-1,8-octanedithiol, ether was added to the reaction solution to precipitate a white powder. After centrifugal separation, the supernatant was removed and the residue was vacuum dried for 3 minutes. After the residue was dissolved in 2.5 ml of DMSO, 0.8 ml of 0.5M TEA was added. The resulting mixture was reacted for 30 minutes for cyclization. The crude peptide thus obtained was purified by HPLC while using a 0.1% trifluoroacetic acid-containing acetonitrile/water concentration gradient.

(2) Synthesis of MCAB-Phe-Ile-Gly-His-Tyr-Arg-Val-His-Pro-Ile-Ser-Leu-Glu-Arg-Cys-Gly (SEQ ID NO: 139)

Solid-phase synthesis was performed through Fmoc/HBTU/HOBt method by placing 0.05 mmol of commercially available Rink Amide-ChemMatrix resin (0.60 mmol/g) in the reactor of a peptide synthesizer Discovery. As a side-chain protecting group of Fmoc amino acid, a Pbf group was used for Arg, a $Bu^t$ group was used for Ser, Glu, and Tyr and a Trt group was used for His and Cys. The Phe-Ile-Gly-His-Tyr-Arg-Val-His-Pro-Ile-Ser-Leu-Glu-Arg-Cys-Gly-resin (SEQ ID NO: 233) (0.025 mmol) thus obtained was treated with 21.4 mg (0.1 mmol) of 3-(2-chloroacetamido) benzoic acid, 37.9 mg (0.1 mmol) of HBTU, 13.5 mg (0.1 mmol) of HOBt, and 17.0 μl (0.2 mmol) of DIEA to introduce a MCAB group.

After the whole portion (0.025 mmol) of the resin was stirred at room temperature for three hours in 1 ml of a mixture (92.5:2.5:2.5:2.5) of TFA, water, triisopropylsilane, and 3,6-dioxa-1,8-octanedithiol, ether was added to the reaction solution to precipitate a white powder. After centrifugal separation, the supernatant was removed and the residue was vacuum dried for 3 minutes. After the residue was dissolved in 2.5 ml of DMSO, 0.8 ml of 0.5M TEA was added. The resulting mixture was reacted for 30 minutes for cyclization. The crude peptide thus obtained was purified by HPLC while using a 0.1% trifluoroacetic acid-containing acetonitrile/water concentration gradient.

A dissociation constant of binding between the cyclic peptide L1 or BL1 thus synthesized and human VEGFR2 or mouse VEGFR2 was determined by BLI method (ForteBio). A fusion protein of VEGFR2 and Fc was immobilized onto Anti-human IgG Capture Biosensors and the cyclic peptide L1 or BL1 varied in concentration was analyzed. The temperature was set at 30° C.

Figure 3:
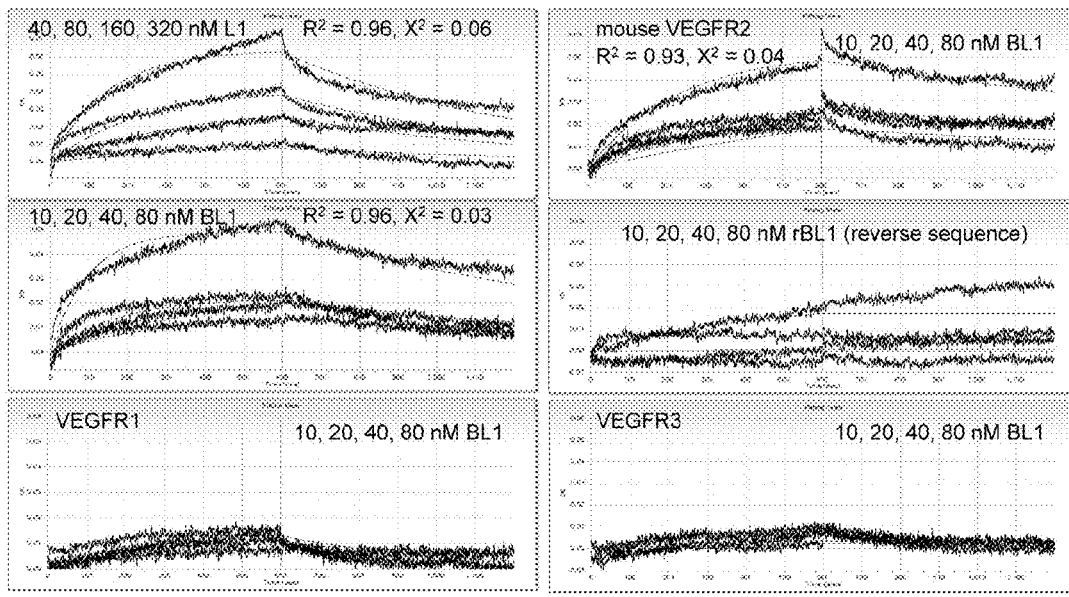
FIG. 3 shows the results of a dissociation constant of binding, as determined by a BLI method (ForteBio), between a VEGFR2-binding cyclic peptide selected by TRAP display method and human VEGFR2 or mouse VEGFR2.

The results are shown in FIG. 3 and the following table.

TABLE 8

Association rate constant, dissociation rate constant, and dissociation constant for human VEGFR2

|  | $k_{on}$ (×10$^6$ Ms$^{-1}$) | $k_{off}$ (×10$^{-3}$ s$^{-1}$) | $K_d$ (nM) |
|---|---|---|---|
| L1 | 0.02 | 2 | 94 |
| BL1 | 0.1 | 0.9 | 8 |

TABLE 9

Association rate constant, dissociation rate constant, and dissociation constant for mouse VEGFR2

|  | $k_{on}$ (×10$^6$ Ms$^{-1}$) | $k_{off}$ (×10$^{-3}$ s$^{-1}$) | $K_d$ (nM) |
|---|---|---|---|
| BL1 | 0.4 | 0.8 | 8 |

The peptide thus selected has high affinity to VEGFR2 and binds to neither VEGFR1 nor VEGFR3 so that it has been verified that it has high specificity to VEGFR2. In addition, the peptide also binds to mouse VEGFR2, suggesting that it can be used even in experiments with animals.

[3] Verification of VEGFR2 Activity Inhibition by L1 or BL1

Next, the VEGFR2 inhibiting activity of the synthesized peptide was confirmed. First, an influence of the peptide on VEGF-dependent VEGFR2 auto-phosphorylation was studied using HUVEC expressing VEGFR2.

A phosphorylation level of VEGFR2 was determined by dot blotting of HUVEC lysate while using an anti-total VEGFR2 antibody and anti-phosphorylation VEGFR2 antibody.

Figure 4:
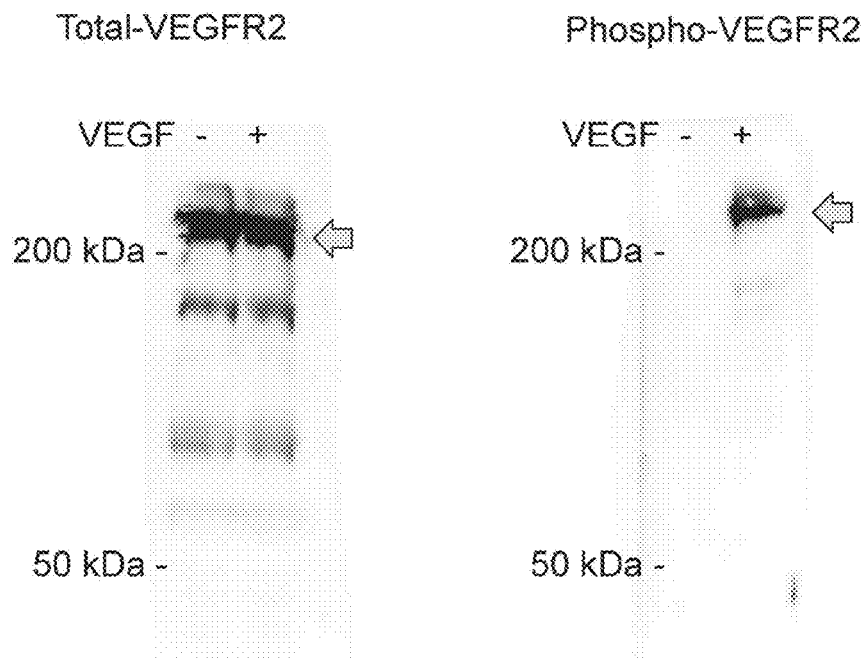
FIG. 4 shows the results, as verified by western blotting, of specificity of an anti-total VEGFR2 antibody that binds to both VEGFR2 and phosphorylated VEGFR2 and an anti-phosphorylated VEGFR2 antibody that binds only to phosphorylated VEGFR2.

First, lysate of HUVEC stimulated or not stimulated with VEGF was separated using 7.5% SDS-PAGE and stained with respective antibodies (results are shown in FIG. 4). It has been confirmed that, by these antibodies, phosphorylated VEGFR2 by stimulation of VEGF and not phosphorylated VEGFR2 were distinguished from each other.

For dot blotting assay, first, HUVEC cells were treated for 15 minutes with L1 or BL1 varied in concentration, followed by treatment for 7 minutes with 10 ng/mL of VEGF. By using the HUVEC lysate, the total VEGFR2 and phosphorylated VEGFR2 were dot blotted with the anti-total VEGFR2 antibody and the anti-phosphorylated VEGFR2 antibody.

Figure 5:
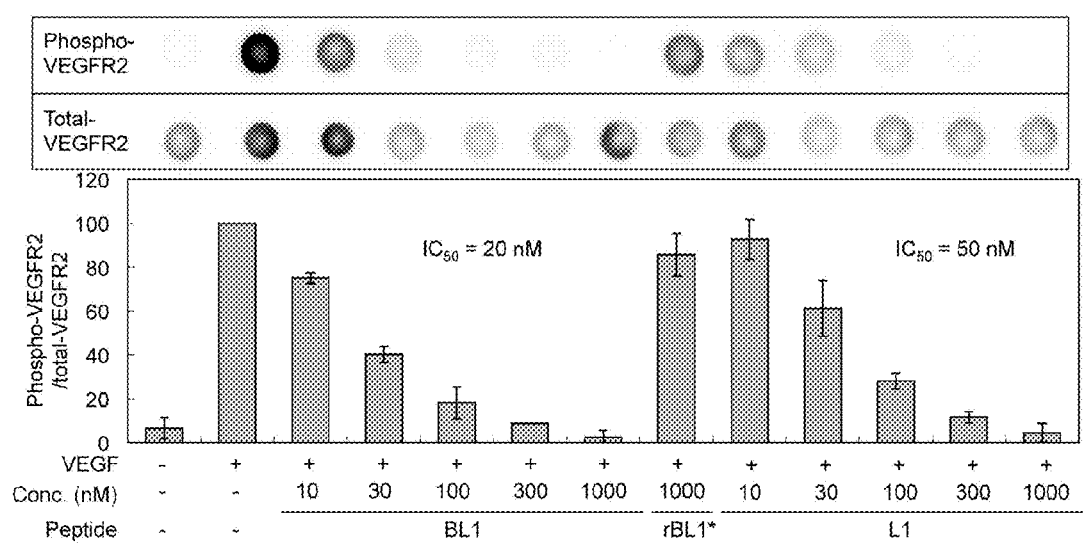
FIG. 5 shows the results, as verified by dot blotting, that the cyclic peptides BL1 and L1 dose-dependently inhibit the auto-phosphorylation of VEGFR2 caused by stimulation with VEGF.

The results of dot blotting are shown in FIG. 5. The error bar represents ±1 s.d. The lysate without peptide and VEGF treatments and the cells without only the peptide treatment are used as control and the phosphorylation rate of the latter one is set at 100%.

It was verified that BL1 and L1 each dose-dependently inhibited auto-phosphorylation of VEGFR2 stimulated with VEGF. With BL1, $IC_{50}=20$ nM and with L1, $IC_{50}=50$ nM.

In this figure, rBL1 means a peptide having a sequence reverse to that of BL1. The rBL1 did not show any phosphorylation inhibiting activity, suggesting that not constituents of the amino acid of the peptide but the sequence thereof are important.

Next, growth inhibiting activity of L1 and BL1 against HUVEC was examined by BrdU method. HUVEC cells were treated for 30 minutes with a cyclic peptide L1 or BL1 varied in concentration and then, co-incubated with the cyclic peptide and 10 ng/mL of VEGF. Twenty four hours later, the cells were labeled with BrdU for 4 hours in the presence of the cyclic peptide and VEGF. Then, the resulting cells were fixed, stained with a peroxidase-conjugated anti-BrdU antibody, and peroxidase activity was detected using a tetramethylbenzidine color colorimetric substrate. The cells without peptide and VEGF treatments and the cells without only peptide treatment were used as a control.

Figure 6:
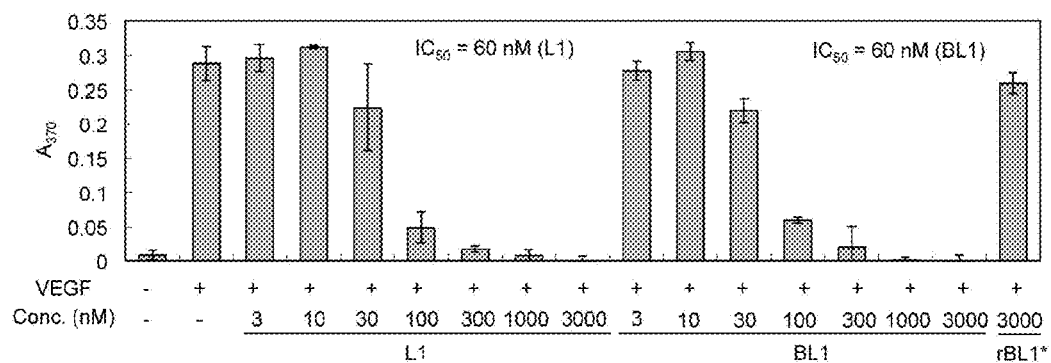
FIG. 6 shows the results of studying, by a BrdU method, the growth inhibitory activity of the cyclic peptides L1 and BL1 against HUVEC.

The results are shown in FIG. 6. The error bar represents ±1 s.d. It was confirmed that the peptides each inhibited growth of HUVEC. With L1, $IC_{50}=60$ nM, while with BL1, $IC_{50}=60$ nM. On the other hand, rBL1, a peptide having a sequence reverse to that of BL1 did not inhibit the growth of HUVEC.

Next, angiogenesis kit of Kurabo was used to study the influence of L1 or BL1 on VEGF-dependent angiogenesis. HUVEC and human skin-derived fibroblasts were co-cultured in the presence of 10 ng/mL of VEGF and L1 or BL1 varied in concentration.

After culturing at 37° C., supplementation with VEGF and peptide having the same concentration three days, six days, and eight days later, and fixation of the HUVEC cells 11 days later, the resulting cells were stained with an anti-CD31 antibody to visualize them and analyzed by making use of an image analysis service included in the kit. As a control, 50 μM of an angiogenesis inhibitor Suramin was added instead of the peptide.

Figure 7:
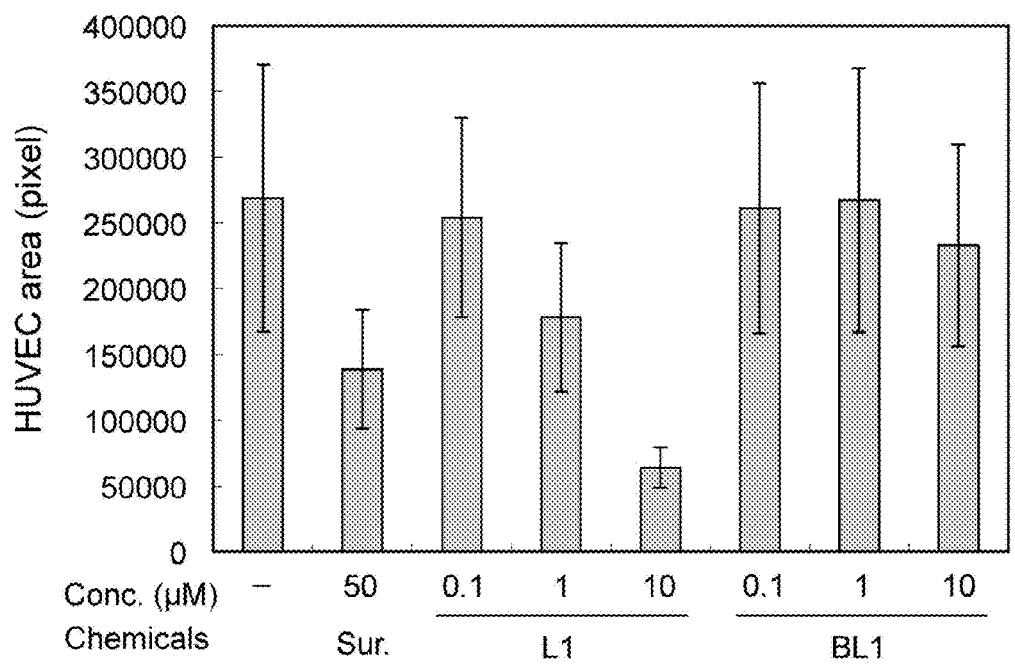
FIG. 7 shows the results of studying the angiogenesis inhibiting effect of the cyclic peptides.

The results are shown in FIG. 7. In the 10 μm-L1 administered group, an angiogenesis inhibiting effect stronger than that of Suramin was observed.

[4] Optimization of Amino Acid Sequence of Peptide

Having confirmed that L1 and BL1 each have highly specific VEGFR2 inhibiting activity, the sequence of L1 and BL1 was next optimized.

(Optimization of L1)

Optimization of L1 was performed by constructing a DNA library encoding a peptide library in which with regard to 15 amino acids except the amino acids at both ends to be used for cyclization, seven amino acids on the C terminal side and eight amino acids on the N terminal side had been randomized and constructing a cyclized peptide library in a manner similar to that employed above in [1] (15 amino acid residues of each peptide except the both-terminal amino acids to be used for cyclization will hereinafter be called, from the N terminal side, $Xaa_1, Xaa_2 \ldots Xaa_{15}$). The peptide sequences selected are shown in FIG. 8 and FIG. 9.

Further, second optimization was performed by constructing, based on the above results, a DNA library encoding a peptide library of L1 in which $Xaa_1$, $Xaa_3$ to $Xaa_5$, $Xaa_9$, and $Xaa_{13}$ to $Xaa_{15}$ had been randomized and constructing a cyclized peptide library in a manner similar to that employed above in [1]. The peptide sequences selected finally by the second optimization are shown in FIG. 10

In the figure, the portion surrounded by a solid line means the sequence that completely converges to the original sequence (sequence of L1). The sequence of this portion is likely to be essential for the binding to VEGFR2. The amino acid surrounded with a dotted line means convergence to a sequence completely non-original. The amino acid of this portion is likely to be more suited for binding to VEGFR2 than the original sequence. The amino acid surrounded with a dashed line means a substitution by a sequence not completely original. The amino acid of this portion is likely to be unimportant in binding to VEGFR2.

In the second optimization procedure, also the following peptides were selected: HVTHQDPWVNGLWIA (SEQ ID NO: 23), VVSHHDPWVNGLFIA (SEQ ID NO: 24), VVVHADPWVNGLWIQ (SEQ ID NO: 25), VVKHPDPWVNGLYFH (SEQ ID NO: 26), VVQHRDPWVNGLWFP (SEQ ID NO: 27), SVVHSDPWVNGLYLS (SEQ ID NO: 28), AVKHSDPWVNGLYLP (SEQ ID NO: 29), SVTHIDPWVNGLYLP (SEQ ID NO: 30), KVSHFDPWVNGLWLP (SEQ ID NO: 31), TVTHRDPWVNGLILS (SEQ ID NO: 32), QVSHPDPWVNGLILQ (SEQ ID NO: 33), TVYSDPWVNGLWLR (SEQ ID NO: 34), SVYGLDPWINGLRFV (SEQ ID NO: 35), TVFHTDPWVNGLWIS (SEQ ID NO: 36), TVRHTDPWVNGLWIS (SEQ ID NO: 37), TVKHPDPWVNGLWIS (SEQ ID NO: 38), TVTHSDPWVNGLFLP (SEQ ID NO: 39), VVTHPDPWVNGLFLP (SEQ ID NO: 40), TVTHIDPWVNGLWLP (SEQ ID NO: 41), TVVHADPWVNGLYLP (SEQ ID NO: 42), TVVHSDPWVNGLWLP (SEQ ID NO: 43), TVIHPDPWVNGLWLP (SEQ ID NO: 44), IVSHPDPWVNGLWLP (SEQ ID NO: 45), SVSHPDPWVNGLWLP (SEQ ID NO: 46), EVSHPDPWVNGLWIP (SEQ ID NO: 47), IVYHADPWVNGLWLS (SEQ ID NO: 48), VVRHSDPWVNGLWID (SEQ ID NO: 49), and VVYSSDPWVNGLHLT (SEQ ID NO: 50).

The tendency of each amino acid residue will next be described.

It has been suggested that various amino acids are allowed as $Xaa_1$, but Val, Thr, or the like is particularly desirable.

It has been suggested that as in the original sequence, $Xaa_2$ completely converges to Val and being Val is necessary for binding to VEGFR2.

It has been suggested that $Xaa_3$ does not show any particular tendency and it is not of high importance in binding to VEGFR2.

Although $Xaa_4$ is Ser in the original sequence, it tends to be His in the sequence after optimization. It may therefore be desirably His, but binding occurs even if it is another amino acid such as Gly or Ser.

It has been suggested that $Xaa_5$ does not show any particular tendency and is not of high importance in binding to VEGFR2.

$Xaa_6$ to $Xaa_8$ converged completely to Asp-Pro-Trp as in the original sequence. Their sequences are likely to be essential for binding to VEGFR2.

It has been suggested that $Xaa_9$ is desirably a hydrophobic aliphatic amino acid and in particular, it is desirably Val.

$Xaa_{10}$ to $Xaa_{12}$ converged completely to Asn-Gly-Leu as in the original sequence. Their sequences are likely to be essential for binding to VEGFR2.

$Xaa_{13}$ is Tyr in the original sequence, but tends to be Trp in the sequence after optimization. It may therefore be desirably Trp, but binding occurs even if it is Ile, Phe, Tyr, or His.

It has been suggested that $Xaa_{14}$ is any of Ile, Leu, and Phe and is desirably a hydrophobic amino acid.

$Xaa_{15}$ is Asp in the original sequence, but various amino acids are allowed in the sequence after optimization. It has been suggested that in particular, it is desirably Pro or Ser.

Peptides in which $Xaa_1$ to $Xaa_{15}$ have the above-mentioned characteristics are highly likely to have VEGFR2 inhibiting activity similar to L1.

(Optimization of BL1)

Optimization of BL1 was also performed as in that of L1 by constructing a DNA library encoding a peptide library in which with regard to 15 amino acids except the amino acids at both ends thereof to be used for cyclization, seven amino acids on the C terminal side and eight amino acids on the N terminal side had been randomized and then constructing a cyclized peptide library by a method similar to that used above in [1] (15 amino acid residues of each peptide except the amino acids at both ends thereof to be used for cyclization will hereinafter be called, from the N terminal side, "$Xaa_{16}$, $Xaa_{17}$ ... $Xaa_{30}$"). The peptide sequences selected are shown in both FIG. 11 and FIG. 12.

Further, second optimization was performed by constructing, based on the above results, a DNA library encoding a peptide library of BL1 in which $Xaa_{16}$ to $Xaa_{20}$, $Xaa_{26}$, and $Xaa_{29}$ to $Xaa_{30}$ had been randomized and constructing a cyclized peptide library in a manner similar to that employed above in [1]. The peptide sequences selected finally by the second optimization are shown in FIG. 13.

A portion surrounded with a heavy line in this figure means that the sequence completely converges to the original sequence (sequence of BL1). The sequence of this portion is likely to be essential for the binding to VEGFR2.

In the second optimization procedure, also the following peptides were selected:

LNGYYVKVHPVSLEP (SEQ ID NO: 97), LNGYRVKVHPISLEP (SEQ ID NO: 98), VGPYAVKVHPISLSP (SEQ ID NO: 99), VGHYRVKVHPISLLP (SEQ ID NO: 100), IGAYKVKVHPISLQP (SEQ ID NO: 101), LGPYRVKVHPISLHF (SEQ ID NO: 102), IGPYLVKVHPVSLHF (SEQ ID NO: 103), IGEYRVKVHPISLAP (SEQ ID NO: 104), IGPYRVKVHPVSLLP (SEQ ID NO: 105), IGIYRVKVHPVSLEP (SEQ ID NO: 106), IGPYAVKVHPVSLEP (SEQ ID NO: 107), IGTWVVKVHPVSLEP (SEQ ID NO: 108), INSYVVKVHPISLEP (SEQ ID NO: 109), ILGYFVKVHPVSLDP (SEQ ID NO: 110), YNGFAVKVHPISLEN (SEQ ID NO: 111), VNGYAVKVHPVSLEP (SEQ ID NO: 112), VNGYIVKVHPVSLEP (SEQ ID NO: 113), IYGFAVKVHPVSLEP (SEQ ID NO: 114), IGIYRVKVHPISLEY (SEQ ID NO: 115), IGIFRVKVHPISLEP (SEQ ID NO: 116), IGIYRVKVHPISLEP (SEQ ID NO: 117), IGRYAVKVHPISLEP (SEQ ID NO: 118), IGPYWVKVHPISLLP (SEQ ID NO: 119), IGPYHVKVHPVSLEP (SEQ ID NO: 120), IGPWFVKVHPVSLEP (SEQ ID NO: 121), IGPYRVKVHPVSLEY (SEQ ID NO: 122), IGPYRVKVHPISLEW (SEQ ID NO: 123), and VNGYRVKVHPISLDW (SEQ ID NO: 124).

The tendency of each amino acid residue will next be described.

It has been suggested that $Xaa_{16}$ is desirably a hydrophobic amino acid. It has been suggested that it is desirably Ile or Val.

As $Xaa_{17}$, various amino acids are allowed and particularly, it tends to be Gly and Asn.

It has been suggested that $Xaa_{18}$ is not of high importance in binding to VEGFR2 because no particular tendency is found.

$Xaa_{19}$ is Tyr, Phe, or Trp, suggesting that it is desirably an aromatic amino acid.

It has been suggested that $Xaa_{20}$ is not of high importance in binding to VEGFR2 because no particular tendency is found.

$Xaa_{21}$ is Ile or Val, suggesting that it is desirably a hydrophobic aliphatic amino acid.

$Xaa_{22}$ is Lys or Arg, suggesting that it is desirably an amino acid having a positive charge.

It has been suggested that $Xaa_{23}$ is desirably a hydrophobic aliphatic amino acid. Particularly, it tends to be Val.

$Xaa_{24}$ and $Xaa_{25}$ each converge completely to His-Pro as in the original sequence. Their sequences are likely to be essential for binding to VEGFR2.

$Xaa_{26}$ is Val or Ile, suggesting that it is desirably a hydrophobic aliphatic amino acid.

$Xaa_{27}$ tends to be Ser and is sometimes Thr or Gly, suggesting that it is desirably a hydrophilic amino acid having no charge.

$Xaa_{28}$ tends to be Leu and is sometimes Phe, suggesting that it is desirably a hydrophobic amino acid.

As $Xaa_{29}$, various amino acids are allowed, but particularly, it tends to be Glu.

As $Xaa_{30}$, various amino acids are allowed, but particularly, it tends to be Pro or an aromatic amino acid.

Peptides in which $Xaa_{16}$ to $Xaa_{30}$ show the above-mentioned characteristics are highly likely to have VEGFR2 inhibiting activity similar to BL1.

The invention claimed is:

1. A peptide comprising the following amino acid sequence:

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$ wherein, $Xaa_2$ represents Val or a derivative thereof, $Xaa_6$ represents Asp or a derivative thereof, $Xaa_7$ represents Pro or a derivative thereof, $Xaa_8$ represents Trp or a derivative thereof, $Xaa_{10}$ represents Asn or a derivative thereof, $Xaa_{11}$ represents Gly or a derivative thereof, $Xaa_{12}$ represents Leu or a derivative thereof, and $Xaa_1$, $Xaa_3$ to $Xaa_5$, $Xaa_9$, and $Xaa_{13}$ to $Xaa_{15}$ each independently represents an arbitrary amino acid or a derivative thereof.

2. The peptide according to claim 1, wherein
$Xaa_1$ represents an arbitrary amino acid or a derivative thereof,
$Xaa_3$ represents an arbitrary amino acid or a derivative thereof,
$Xaa_4$ is selected from Gly, His, and Ser, and derivatives thereof,
$Xaa_5$ represents an arbitrary amino acid or a derivative thereof,
$Xaa_9$ is selected from aliphatic amino acids and derivatives thereof,
$Xaa_{13}$ represents an arbitrary amino acid or a derivative thereof,
$Xaa_{14}$ is selected from hydrophobic amino acids and derivatives thereof, and
$Xaa_{15}$ represents an arbitrary amino acid or a derivative thereof.

3. The peptide according to claim 1, wherein
$Xaa_1$ is selected from Val and Thr, and derivatives thereof,
$Xaa_3$ represents an arbitrary amino acid or a derivative thereof,
$Xaa_4$ represents His or a derivative thereof,
$Xaa_5$ represents an arbitrary amino acid or a derivative thereof,
$Xaa_9$ represents Val or a derivative thereof,
$Xaa_{13}$ represents an aromatic amino acid or a derivative thereof,
$Xaa_{14}$ is selected from Phe, Leu, and Ile and derivatives thereof, and
$Xaa_{15}$ is selected from Pro and Ser and derivatives thereof.

4. The peptide according to claim 1, wherein $Xaa_1$-$Xaa_2$-$Xaa_3$-$Xaa_4$-$Xaa_5$-$Xaa_6$-$Xaa_7$-$Xaa_8$ is selected from the group consisting of VVRHTDPW (SEQ ID NO: 1), VVVHTDPW (SEQ ID NO: 2), VVRHNDPW (SEQ ID NO: 3), VVSHPDPW (SEQ ID NO: 4), VVSHHDPW (SEQ ID NO: 5), VVKHSDPW (SEQ ID NO: 6), VVKHPDPW (SEQ ID NO: 7), IVRHPDPW (SEQ ID NO: 8), IVTHSDPW (SEQ ID NO: 9), VVTHSDPW (SEQ ID NO: 10), TVTHTDPW (SEQ ID NO: 11), TVKHTDPW (SEQ ID NO: 12), TVRHTDPW (SEQ ID NO: 13), TVYHSDPW (SEQ ID NO: 14), and VVVSTDPW (SEQ ID NO: 15).

5. The peptide according to claim 1, wherein $Xaa_9$-$Xaa_{10}$-$Xaa_{11}$-$Xaa_{12}$-$Xaa_{13}$-$Xaa_{14}$-$Xaa_{15}$ is selected from the group consisting of VNGLWLR (SEQ ID NO: 16), VNGLWFP (SEQ ID NO: 17), VNGLWFY (SEQ ID NO: 18), VNGLWLW (SEQ ID NO: 19), VNGLWLQ (SEQ ID NO: 20), ANGLWLA (SEQ ID NO: 21), and VNGLYLD (SEQ ID NO: 22).

6. The peptide according to claim 1, wherein $Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$ is selected from the group consisting of HVTHQDPWVNGLWIA (SEQ ID NO: 23), VVSHHDPWVNGLFIA (SEQ ID NO: 24), VVVHADPWVNGLWIQ (SEQ ID NO: 25), VVKHPDPWVNGLYFH (SEQ ID NO: 26), VVQHRDPWVNGLWFP (SEQ ID NO: 27), SVVHSDPWVNGLYLS (SEQ ID NO: 28), AVKHSDPWVNGLYLP (SEQ ID NO: 29), SVTHIDPWVNGLYLP (SEQ ID NO: 30), KVSHFDPWVNGLWLP (SEQ ID NO: 31), TVTHRDPWVNGLILS (SEQ ID NO: 32), QVSHPDPWVNGLILQ (SEQ ID NO: 33), TVYSDDPWVNGLWLR (SEQ ID NO: 34), SVYGLDPWINGLRFV (SEQ ID NO: 35), TVFHTDPWVNGLWIS (SEQ ID NO: 36), TVRHTDPWVNGLWIS (SEQ ID NO: 37), TVKHPDPWVNGLWIS (SEQ ID NO: 38), TVTHSDPWVNGLFLP (SEQ ID NO: 39), VVTHPDPWVNGLFLP (SEQ ID NO: 40), TVTHIDPWVNGLWLP (SEQ ID NO: 41), TVVHADPWVNGLYLP (SEQ ID NO: 42), TVVHSDPWVNGLWLP (SEQ ID NO: 43), TVIHPDPWVNGLWLP (SEQ ID NO: 44), IVSHPDPWVNGLWLP (SEQ ID NO: 45), SVSHPDPWVNGLWLP (SEQ ID NO: 46), EVSHPDPWVNGLWIP (SEQ ID NO: 47), IVYHADPWVNGLWLS (SEQ ID NO: 48), VVRHSDPWVNGLWID (SEQ ID NO: 49), VVYSSDPWVNGLHLT (SEQ ID NO: 50), TVSHPDPWVNGLWIR (SEQ ID NO: 51), TVYHPDPWVNGLWIR (SEQ ID NO: 52), TVWHPDPWVNGLWIY (SEQ ID NO: 53), EVKHPDPWVNGLWIY (SEQ ID NO: 54), TVVHPDPWVNGLWIS (SEQ ID NO: 55), TVRHPDPWVNGLWLS (SEQ ID NO: 56), TVRHPDPWVNGLWFS (SEQ ID NO: 57), TVSHPDPWVNGLWLQ (SEQ ID NO: 58), TVTHPDPWVNGLWLP (SEQ ID NO: 59), TVTHPDPWVNGLYLP (SEQ ID NO: 60), TVYHPDPWVNGLWLP (SEQ ID NO: 61), TVVHPDPWVNGLWLP (SEQ ID NO: 62), TVFHPDPWVNGLWIP (SEQ ID NO: 63), AVTHSDPWVNGLWLP (SEQ ID NO: 64), TVTHSDPWVNGLWFP (SEQ ID NO: 65), EVSHPDPWVNGLWFP (SEQ ID NO: 66), AVSHPDPWVNGLWFP (SEQ ID NO: 67), and SVVHHDPWVNGLWFP (SEQ ID NO: 68).

7. A peptide comprising an amino acid sequence obtained by deleting, adding, or substituting up to five amino acids in the amino acid sequence of the peptide as claimed in claim 1 and having inhibiting activity against a vascular endothelial growth factor receptor VEGFR2.

8. A pharmaceutical comprising the peptide as claimed in claim 1.

* * * * *

SEQUENCE LISTING

<160> NUMBER OF SEQ ID NOS: 233

<210> SEQ ID NO 1
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 1

Val Val Arg His Thr Asp Pro Trp
1               5

<210> SEQ ID NO 2
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 2

Val Val Val His Thr Asp Pro Trp
1               5

<210> SEQ ID NO 3
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 3

Val Val Arg His Asn Asp Pro Trp
1               5

<210> SEQ ID NO 4
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 4

Val Val Ser His Pro Asp Pro Trp
1               5

<210> SEQ ID NO 5
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 5

Val Val Ser His His Asp Pro Trp
1               5

<210> SEQ ID NO 6
<211> LENGTH: 8
<212> TYPE: PRT
<213> ORGANISM: Artificial Sequence
<220> FEATURE:
<223> OTHER INFORMATION: Synthesized peptide (an example of

```
                                      -continued
        Xaa1-Xaa2-Xaa3-Xaa4-Xaa5-Xaa6-Xaa7-Xaa8).

<400> SEQUENCE: 6

Val Val Lys His Ser Asp Pro Trp
1               5

<210> SEQ ID NO 7
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 7

Val Val Lys His Pro Asp Pro Trp
1               5

<210> SEQ ID NO 8
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 8

Ile Val Arg His Pro Asp Pro Trp
1               5

<210> SEQ ID NO 9
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 9

Ile Val Thr His Ser Asp Pro Trp
1               5

<210> SEQ ID NO 10
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 10

Val Val Thr His Ser Asp Pro Trp
1               5

<210> SEQ ID NO 11
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 11

Thr Val Thr His Thr Asp Pro Trp
1               5

<210> SEQ ID NO 12
```

```
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 12

Thr Val Lys His Thr Asp Pro Trp
1               5

<210> SEQ ID NO 13
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 13

Thr Val Arg His Thr Asp Pro Trp
1               5

<210> SEQ ID NO 14
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 14

Thr Val Tyr His Ser Asp Pro Trp
1               5

<210> SEQ ID NO 15
<211> LENGTH: 8
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8).

<400> SEQUENCE: 15

Val Val Val Ser Thr Asp Pro Trp
1               5

<210> SEQ ID NO 16
<211> LENGTH: 7
<212> TYPE: PRT
<213> ORGANISM: Artificial Sequence
<220> FEATURE:
<223> OTHER INFORMATION: Synthesized peptide (an example of
      Xaa9-Xaa10-Xaa11-Xaa12-Xaa13-Xaa14-Xaa15).

<400> SEQUENCE: 16

Val Asn Gly Leu Trp Leu Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthesized peptide (an example of
      Xaa9-Xaa10-Xaa11-Xaa12-Xaa13-Xaa14-Xaa15).

<400> SEQUENCE: 17
```

```
Val Asn Gly Leu Trp Phe Pro
1               5

<210> SEQ ID NO 18
<211> LENGTH: 7
<212> TYPE: PRT
<213> ORGANISM: Artificial Sequence
<220> FEATURE:
<223> OTHER INFORMATION: Synthesized peptide (an example of
      Xaa9-Xaa10-Xaa11-Xaa12-Xaa13-Xaa14-Xaa15).

<400> SEQUENCE: 18

Val Asn Gly Leu Trp Phe Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthesized peptide (an example of
      Xaa9-Xaa10-Xaa11-Xaa12-Xaa13-Xaa14-Xaa15).

<400> SEQUENCE: 19

Val Asn Gly Leu Trp Leu Trp
1               5

<210> SEQ ID NO 20
<211> LENGTH: 7
<212> TYPE: PRT
<213> ORGANISM: Artificial Sequence
<220> FEATURE:
<223> OTHER INFORMATION: Synthesized peptide (an example of
      Xaa9-Xaa10-Xaa11-Xaa12-Xaa13-Xaa14-Xaa15).

<400> SEQUENCE: 20

Val Asn Gly Leu Trp Leu Gln
1               5

<210> SEQ ID NO 21
<211> LENGTH: 7
<212> TYPE: PRT
<213> ORGANISM: Artificial Sequence
<220> FEATURE:
<223> OTHER INFORMATION: Synthesized peptide (an example of
      Xaa9-Xaa10-Xaa11-Xaa12-Xaa13-Xaa14-Xaa15).

<400> SEQUENCE: 21

Ala Asn Gly Leu Trp Leu Ala
1               5

<210> SEQ ID NO 22
<211> LENGTH: 7
<212> TYPE: PRT
<213> ORGANISM: Artificial Sequence
<220> FEATURE:
<223> OTHER INFORMATION: Synthesized peptide (an example of
      Xaa9-Xaa10-Xaa11-Xaa12-Xaa13-Xaa14-Xaa15).

<400> SEQUENCE: 22

Val Asn Gly Leu Tyr Leu Asp
1               5

<210> SEQ ID NO 23
<211> LENGTH: 15
<212> TYPE: PRT
<213> ORGANISM: Artificial Sequence
<220> FEATURE:
```

```
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 23

His Val Thr His Gln Asp Pro Trp Val Asn Gly Leu Trp Ile Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 24

Val Val Ser His His Asp Pro Trp Val Asn Gly Leu Phe Ile Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 25

Val Val Val His Ala Asp Pro Trp Val Asn Gly Leu Trp Ile Gln
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 26

Val Val Lys His Pro Asp Pro Trp Val Asn Gly Leu Tyr Phe His
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 27

Val Val Gln His Arg Asp Pro Trp Val Asn Gly Leu Trp Phe Pro
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).
```

```
<400> SEQUENCE: 28

Ser Val Val His Ser Asp Pro Trp Val Asn Gly Leu Tyr Leu Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 29

Ala Val Lys His Ser Asp Pro Trp Val Asn Gly Leu Tyr Leu Pro
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 30

Ser Val Thr His Ile Asp Pro Trp Val Asn Gly Leu Tyr Leu Pro
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 31

Lys Val Ser His Phe Asp Pro Trp Val Asn Gly Leu Trp Leu Pro
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 32

Thr Val Thr His Arg Asp Pro Trp Val Asn Gly Leu Ile Leu Ser
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 33

Gln Val Ser His Pro Asp Pro Trp Val Asn Gly Leu Ile Leu Gln
1               5                   10                  15
```

```
<210> SEQ ID NO 34
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 34

Thr Val Tyr Ser Asp Asp Pro Trp Val Asn Gly Leu Trp Leu Arg
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 35

Ser Val Tyr Gly Leu Asp Pro Trp Ile Asn Gly Leu Arg Phe Val
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 36

Thr Val Phe His Thr Asp Pro Trp Val Asn Gly Leu Trp Ile Ser
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 37

Thr Val Arg His Thr Asp Pro Trp Val Asn Gly Leu Trp Ile Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 38

Thr Val Lys His Pro Asp Pro Trp Val Asn Gly Leu Trp Ile Ser
1               5                   10                  15

<210> SEQ ID NO 39
<211> LENGTH: 15
```

-continued

```
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 39

Thr Val Thr His Ser Asp Pro Trp Val Asn Gly Leu Phe Leu Pro
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 40

Val Val Thr His Pro Asp Pro Trp Val Asn Gly Leu Phe Leu Pro
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 41

Thr Val Thr His Ile Asp Pro Trp Val Asn Gly Leu Trp Leu Pro
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 42

Thr Val Val His Ala Asp Pro Trp Val Asn Gly Leu Tyr Leu Pro
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 43

Thr Val Val His Ser Asp Pro Trp Val Asn Gly Leu Trp Leu Pro
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthesized peptide (an example of
```

```
Xaa1-Xaa2-Xaa3-Xaa4-Xaa5-Xaa6-Xaa7-Xaa8-Xaa9-Xaa10-Xaa11-Xaa12-
Xaa13-Xaa14-Xaa15).

<400> SEQUENCE: 44

Thr Val Ile His Pro Asp Pro Trp Val Asn Gly Leu Trp Leu Pro
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 45

Ile Val Ser His Pro Asp Pro Trp Val Asn Gly Leu Trp Leu Pro
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 46

Ser Val Ser His Pro Asp Pro Trp Val Asn Gly Leu Trp Leu Pro
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 47

Glu Val Ser His Pro Asp Pro Trp Val Asn Gly Leu Trp Ile Pro
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 48

Ile Val Tyr His Ala Asp Pro Trp Val Asn Gly Leu Trp Leu Ser
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 49
```

```
Val Val Arg His Ser Asp Pro Trp Val Asn Gly Leu Trp Ile Asp
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 50

Val Val Tyr Ser Ser Asp Pro Trp Val Asn Gly Leu His Leu Thr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 51

Thr Val Ser His Pro Asp Pro Trp Val Asn Gly Leu Trp Ile Arg
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 52

Thr Val Tyr His Pro Asp Pro Trp Val Asn Gly Leu Trp Ile Arg
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 53

Thr Val Trp His Pro Asp Pro Trp Val Asn Gly Leu Trp Ile Tyr
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 54

Glu Val Lys His Pro Asp Pro Trp Val Asn Gly Leu Trp Ile Tyr
1               5                   10                  15
```

<210> SEQ ID NO 55
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 55

Thr Val Val His Pro Asp Pro Trp Val Asn Gly Leu Trp Ile Ser
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 56

Thr Val Arg His Pro Asp Pro Trp Val Asn Gly Leu Trp Leu Ser
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 57

Thr Val Arg His Pro Asp Pro Trp Val Asn Gly Leu Trp Phe Ser
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 58

Thr Val Ser His Pro Asp Pro Trp Val Asn Gly Leu Trp Leu Gln
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 59

Thr Val Thr His Pro Asp Pro Trp Val Asn Gly Leu Trp Leu Pro
1               5                   10                  15

<210> SEQ ID NO 60
<211> LENGTH: 15
<212> TYPE: PRT

```
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 60

Thr Val Thr His Pro Asp Pro Trp Val Asn Gly Leu Tyr Leu Pro
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 61

Thr Val Tyr His Pro Asp Pro Trp Val Asn Gly Leu Trp Leu Pro
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 62

Thr Val Val His Pro Asp Pro Trp Val Asn Gly Leu Trp Leu Pro
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 63

Thr Val Phe His Pro Asp Pro Trp Val Asn Gly Leu Trp Ile Pro
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 64

Ala Val Thr His Ser Asp Pro Trp Val Asn Gly Leu Trp Leu Pro
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
```

```
Xaa13-Xaa14-Xaa15).

<400> SEQUENCE: 65

Thr Val Thr His Ser Asp Pro Trp Val Asn Gly Leu Trp Phe Pro
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 66

Glu Val Ser His Pro Asp Pro Trp Val Asn Gly Leu Trp Phe Pro
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 67

Ala Val Ser His Pro Asp Pro Trp Val Asn Gly Leu Trp Phe Pro
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthesized peptide (an example of
      Xaa1-Xaa2-Xaa3-Xaa4-Xaa5-Xaa6-Xaa7-Xaa8-Xaa9-Xaa10-Xaa11-Xaa12-
      Xaa13-Xaa14-Xaa15).

<400> SEQUENCE: 68

Ser Val Val His His Asp Pro Trp Val Asn Gly Leu Trp Phe Pro
1               5                   10                  15

<210> SEQ ID NO 69
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 69

Val Asn Gly Tyr Arg Val Lys Val
1               5

<210> SEQ ID NO 70
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 70

Val Asn Gly Tyr Ser Ile Lys Val
1               5
```

<210> SEQ ID NO 71
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 71

Ile Asn Gly Tyr Lys Ile Lys Val
1               5

<210> SEQ ID NO 72
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 72

Ile Gly Pro Tyr Lys Ile Arg Val
1               5

<210> SEQ ID NO 73
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 73

Ile Gly Pro Tyr Arg Ile Arg Leu
1               5

<210> SEQ ID NO 74
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 74

Tyr Gly Pro Tyr Ala Ile Lys Val
1               5

<210> SEQ ID NO 75
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 75

Ile Gly Pro Tyr Val Ile Lys Val
1               5

<210> SEQ ID NO 76
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

-continued

<400> SEQUENCE: 76

Ile Gly Arg Phe Arg Ile Lys Val
1               5

<210> SEQ ID NO 77
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 77

Leu Gly Arg Trp Ser Ile Lys Val
1               5

<210> SEQ ID NO 78
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 78

Ile Gly Ser Phe Val Ile Arg Val
1               5

<210> SEQ ID NO 79
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 79

Ile Arg Gly Phe Arg Ile Arg Val
1               5

<210> SEQ ID NO 80
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 80

Val Gly Pro Tyr Arg Ile Arg Val
1               5

<210> SEQ ID NO 81
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 81

Val Gly Ile Tyr Gln Ile Arg Val
1               5

<210> SEQ ID NO 82
<211> LENGTH: 8

```
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 82

Ile Gly His Tyr Arg Val Lys Val
1               5

<210> SEQ ID NO 83
<211> LENGTH: 8
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23).

<400> SEQUENCE: 83

Ile Gly His Tyr Arg Val Lys Val
1               5

<210> SEQ ID NO 84
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 84

His Pro Ile Ser Leu Ala Pro
1               5

<210> SEQ ID NO 85
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 85

His Pro Ile Ser Leu Ser Pro
1               5

<210> SEQ ID NO 86
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 86

His Pro Ile Ser Leu Glu Pro
1               5

<210> SEQ ID NO 87
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 87

His Pro Ile Ser Leu Glu Tyr
```

```
1               5
```

<210> SEQ ID NO 88
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 88

```
His Pro Ile Ser Leu Glu Trp
1               5
```

<210> SEQ ID NO 89
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 89

```
His Pro Ile Ser Leu Leu Pro
1               5
```

<210> SEQ ID NO 90
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 90

```
His Pro Val Ser Leu Glu Pro
1               5
```

<210> SEQ ID NO 91
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 91

```
His Pro Val Ser Phe Glu Pro
1               5
```

<210> SEQ ID NO 92
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 92

```
His Pro Val Ser Leu Glu Ser
1               5
```

<210> SEQ ID NO 93
<211> LENGTH: 7
<212> TYPE: PRT
<213> ORGANISM: Artificial Sequence
<220> FEATURE:
<223> OTHER INFORMATION: Synthesized peptide (an example of -continued Xaa24-Xaa25-Xaa26-Xaa27-Xaa28-Xaa29-Xaa30).

<400> SEQUENCE: 93

His Pro Val Ser Leu Glu Tyr
1               5

<210> SEQ ID NO 94
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 94

His Pro Val Thr Leu Ala Trp
1               5

<210> SEQ ID NO 95
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 95

His Pro Val Gly Leu Trp Pro
1               5

<210> SEQ ID NO 96
<211> LENGTH: 7
<212> TYPE: PRT
<213> ORGANISM: Artificial Sequence
<220> FEATURE:
<223> OTHER INFORMATION: Synthesized peptide (an example of
      Xaa24-Xaa25-Xaa26-Xaa27-Xaa28-Xaa29-Xaa30).

<400> SEQUENCE: 96

His Pro Ile Ser Leu Glu Arg
1               5

<210> SEQ ID NO 97
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 97

Leu Asn Gly Tyr Tyr Val Lys Val His Pro Val Ser Leu Glu Pro
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 98

Leu Asn Gly Tyr Arg Val Lys Val His Pro Ile Ser Leu Glu Pro
1               5                   10                  15

-continued

```
<210> SEQ ID NO 99
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 99

Val Gly Pro Tyr Ala Val Lys Val His Pro Ile Ser Leu Ser Pro
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 100

Val Gly His Tyr Arg Val Lys Val His Pro Ile Ser Leu Leu Pro
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 101

Ile Gly Ala Tyr Lys Val Lys Val His Pro Ile Ser Leu Gln Pro
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 102

Leu Gly Pro Tyr Arg Val Lys Val His Pro Ile Ser Leu His Phe
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 103

Ile Gly Pro Tyr Leu Val Lys Val His Pro Val Ser Leu His Phe
1               5                   10                  15

<210> SEQ ID NO 104
<211> LENGTH: 15
<212> TYPE: PRT
```

<213> ORGANISM: Artificial Sequence
<220> FEATURE:
<223> OTHER INFORMATION: Synthesized peptide (an example of
    Xaa16-Xaa17-Xaa18-Xaa19-Xaa20-Xaa21-Xaa22-Xaa23-Xaa24-Xaa25-Xaa26-
    Xaa27-Xaa28-Xaa29-Xaa30).

<400> SEQUENCE: 104

Ile Gly Glu Tyr Arg Val Lys Val His Pro Ile Ser Leu Ala Pro
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthesized peptide (an example of
    Xaa16-Xaa17-Xaa18-Xaa19-Xaa20-Xaa21-Xaa22-Xaa23-Xaa24-Xaa25-Xaa26-
    Xaa27-Xaa28-Xaa29-Xaa30).

<400> SEQUENCE: 105

Ile Gly Pro Tyr Arg Val Lys Val His Pro Val Ser Leu Leu Pro
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Synthesized peptide (an example of
    Xaa16-Xaa17-Xaa18-Xaa19-Xaa20-Xaa21-Xaa22-Xaa23-Xaa24-Xaa25-Xaa26-
    Xaa27-Xaa28-Xaa29-Xaa30).

<400> SEQUENCE: 106

Ile Gly Ile Tyr Arg Val Lys Val His Pro Val Ser Leu Glu Pro
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthesized peptide (an example of
    Xaa16-Xaa17-Xaa18-Xaa19-Xaa20-Xaa21-Xaa22-Xaa23-Xaa24-Xaa25-Xaa26-
    Xaa27-Xaa28-Xaa29-Xaa30).

<400> SEQUENCE: 107

Ile Gly Pro Tyr Ala Val Lys Val His Pro Val Ser Leu Glu Pro
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthesized peptide (an example of
    Xaa16-Xaa17-Xaa18-Xaa19-Xaa20-Xaa21-Xaa22-Xaa23-Xaa24-Xaa25-Xaa26-
    Xaa27-Xaa28-Xaa29-Xaa30).

<400> SEQUENCE: 108

Ile Gly Thr Trp Val Val Lys Val His Pro Val Ser Leu Glu Pro
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthesized peptide (an example of
    Xaa16-Xaa17-Xaa18-Xaa19-Xaa20-Xaa21-Xaa22-Xaa23-Xaa24-Xaa25-Xaa26-

-continued

Xaa27-Xaa28-Xaa29-Xaa30).

<400> SEQUENCE: 109

Ile Asn Ser Tyr Val Val Lys Val His Pro Ile Ser Leu Glu Pro
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 110

Ile Leu Gly Tyr Phe Val Lys Val His Pro Val Ser Leu Asp Pro
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 111

Tyr Asn Gly Phe Ala Val Lys Val His Pro Ile Ser Leu Glu Asn
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 112

Val Asn Gly Tyr Ala Val Lys Val His Pro Val Ser Leu Glu Pro
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 113

Val Asn Gly Tyr Ile Val Lys Val His Pro Val Ser Leu Glu Pro
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 114

Ile Tyr Gly Phe Ala Val Lys Val His Pro Val Ser Leu Glu Pro
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 115

Ile Gly Ile Tyr Arg Val Lys Val His Pro Ile Ser Leu Glu Tyr
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 116

Ile Gly Ile Phe Arg Val Lys Val His Pro Ile Ser Leu Glu Pro
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 117

Ile Gly Ile Tyr Arg Val Lys Val His Pro Ile Ser Leu Glu Pro
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 118

Ile Gly Arg Tyr Ala Val Lys Val His Pro Ile Ser Leu Glu Pro
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 119

Ile Gly Pro Tyr Trp Val Lys Val His Pro Ile Ser Leu Leu Pro
1               5                   10                  15

-continued

```
<210> SEQ ID NO 120
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 120

Ile Gly Pro Tyr His Val Lys Val His Pro Val Ser Leu Glu Pro
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 121

Ile Gly Pro Trp Phe Val Lys Val His Pro Val Ser Leu Glu Pro
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 122

Ile Gly Pro Tyr Arg Val Lys Val His Pro Val Ser Leu Glu Tyr
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 123

Ile Gly Pro Tyr Arg Val Lys Val His Pro Ile Ser Leu Glu Trp
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 124

Val Asn Gly Tyr Arg Val Lys Val His Pro Ile Ser Leu Asp Trp
1               5                   10                  15

<210> SEQ ID NO 125
<211> LENGTH: 15
<212> TYPE: PRT
<213> ORGANISM: Artificial Sequence
```

-continued

```
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 125

Leu Tyr Gly Tyr Arg Val Lys Val His Pro Ile Ser Leu Glu Pro
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 126

Ile Gly Ile Tyr Arg Val Lys Val His Pro Ile Ser Leu Glu Pro
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 127

Ile Gly Pro Tyr Arg Val Lys Val His Pro Ile Ser Leu Glu Pro
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 128

Ile Gly Pro Tyr Trp Val Lys Val His Pro Ile Ser Leu Glu Pro
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 129

Ile Gly Pro Tyr Arg Val Lys Val His Pro Val Ser Leu Glu Pro
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).
```

```
<400> SEQUENCE: 130

Ile Gly Pro Tyr Arg Ile Lys Val His Pro Val Ser Leu Glu Pro
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 131

Val Gly Pro Tyr Arg Val Lys Val His Pro Val Ser Leu Glu Pro
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 132

Ile Gly Pro Tyr Val Val Lys Val His Pro Val Ser Leu Glu Pro
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 133

Ile Gly Pro Tyr Arg Val Lys Val His Pro Val Ser Leu Glu Tyr
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 134

Ile Gly Pro Tyr Trp Val Lys Val His Pro Val Ser Leu Glu Trp
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Synthesized peptide (an example of
      Xaa16-Xaa17-Xaa18-Xaa19-Xaa20-Xaa21-Xaa22-Xaa23-Xaa24-Xaa25-Xaa26-
      Xaa27-Xaa28-Xaa29-Xaa30).

<400> SEQUENCE: 135

Ile Asn Gly Tyr Tyr Val Lys Val His Pro Val Ser Leu Asp Trp
```

<210> SEQ ID NO 136
<211> LENGTH: 17
<212> TYPE: PRT
<213> ORGANISM: Artificial Sequence
<220> FEATURE:
<223> OTHER INFORMATION: Synthesized peptide L1.
<220> FEATURE:
<221> NAME/KEY: MISC_FEATURE
<222> LOCATION: (1)..(1)
<223> OTHER INFORMATION: N-chloroacetyl-L-phenylalanine.

<400> SEQUENCE: 136

Phe Val Val Val Ser Thr Asp Pro Trp Val Asn Gly Leu Tyr Ile Asp
1               5                   10                  15

Cys

<210> SEQ ID NO 137
<211> LENGTH: 17
<212> TYPE: PRT
<213> ORGANISM: Artificial Sequence
<220> FEATURE:
<223> OTHER INFORMATION: Synthesized peptide BL1
<220> FEATURE:
<221> NAME/KEY: MISC_FEATURE
<222> LOCATION: (1)..(1)
<223> OTHER INFORMATION: MCAB-L-phenylalanine.

<400> SEQUENCE: 137

Phe Ile Gly His Tyr Arg Val Lys Val His Pro Ile Ser Leu Glu Arg
1               5                   10                  15

Cys

<210> SEQ ID NO 138
<211> LENGTH: 18
<212> TYPE: PRT
<213> ORGANISM: Artificial Sequence
<220> FEATURE:
<223> OTHER INFORMATION: Peptide L1 prepared by solid-phase synthesis.
<220> FEATURE:
<221> NAME/KEY: MISC_FEATURE
<222> LOCATION: (1)..(1)
<223> OTHER INFORMATION: N-chloroacetyl-L-phenylalanine.

<400> SEQUENCE: 138

Phe Val Val Val Ser Thr Asp Pro Trp Val Asn Gly Leu Tyr Ile Asp
1               5                   10                  15

Cys Gly

<210> SEQ ID NO 139
<211> LENGTH: 16
<212> TYPE: PRT
<213> ORGANISM: Artificial Sequence
<220> FEATURE:
<223> OTHER INFORMATION: Peptide BL1 prepared by solid-phase synthesis.
<220> FEATURE:
<221> NAME/KEY: MISC_FEATURE
<222> LOCATION: (1)..(1)
<223> OTHER INFORMATION: MCAB-L-phenylalanine.

<400> SEQUENCE: 139

Phe Ile Gly His Tyr Arg Val His Pro Ile Ser Leu Glu Arg Cys Gly
1               5                   10                  15

<210> SEQ ID NO 140
<211> LENGTH: 15

```
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: MISC_FEATURE
<222> LOCATION: (1)..(1)
<223> OTHER INFORMATION: Xaa is any amino acid residue or a derivative
      thereof.
<220> FEATURE:
<221> NAME/KEY: MISC_FEATURE
<222> LOCATION: (2)..(2)
<223> OTHER INFORMATION: Xaa is Val or a derivative thereof.
<220> FEATURE:
<221> NAME/KEY: MISC_FEATURE
<222> LOCATION: (3)..(5)
<223> OTHER INFORMATION: Xaa is any amino acid residue or a derivative
      thereof.
<220> FEATURE:
<221> NAME/KEY: MISC_FEATURE
<222> LOCATION: (6)..(6)
<223> OTHER INFORMATION: Xaa is Asp or a derivative thereo.
<220> FEATURE:
<221> NAME/KEY: MISC_FEATURE
<222> LOCATION: (7)..(7)
<223> OTHER INFORMATION: Xaa is Pro or a derivative thereo.
<220> FEATURE:
<221> NAME/KEY: MISC_FEATURE
<222> LOCATION: (8)..(8)
<223> OTHER INFORMATION: Xaa is Trp or a derivative thereo.
<220> FEATURE:
<221> NAME/KEY: MISC_FEATURE
<222> LOCATION: (9)..(9)
<223> OTHER INFORMATION: Xaa is any amino acid residue or a derivative
      thereof.
<220> FEATURE:
<221> NAME/KEY: MISC_FEATURE
<222> LOCATION: (10)..(10)
<223> OTHER INFORMATION: Xaa is Asn or a derivative thereof.
<220> FEATURE:
<221> NAME/KEY: MISC_FEATURE
<222> LOCATION: (11)..(11)
<223> OTHER INFORMATION: Xaa is Gly or a derivative thereof.
<220> FEATURE:
<221> NAME/KEY: MISC_FEATURE
<222> LOCATION: (12)..(12)
<223> OTHER INFORMATION: Xaa is Leu or a derivative thereof.
<220> FEATURE:
<221> NAME/KEY: MISC_FEATURE
<222> LOCATION: (13)..(15)
<223> OTHER INFORMATION: Xaa is any amino acid residue or a derivative
      thereof.

<400> SEQUENCE: 140

Xaa Xaa Xaa Xaa Xaa Xaa Xaa Xaa Xaa Xaa Xaa Xaa Xaa Xaa Xaa
1               5                   10                  15

<210> SEQ ID NO 141
<211> LENGTH: 8
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: MISC_FEATURE
<222> LOCATION: (1)..(1)
<223> OTHER INFORMATION: Xaa is any amino acid residue or a derivative
      thereof.
<220> FEATURE:
<221> NAME/KEY: MISC_FEATURE
<222> LOCATION: (2)..(2)
<223> OTHER INFORMATION: Xaa is Val or a derivative thereof.
<220> FEATURE:
<221> NAME/KEY: MISC_FEATURE
<222> LOCATION: (3)..(5)
<223> OTHER INFORMATION: Xaa is any amino acid residue or a derivative
      thereof.
```

```
<220> FEATURE:
<221> NAME/KEY: MISC_FEATURE
<222> LOCATION: (6)..(6)
<223> OTHER INFORMATION: Xaa is Asp or a derivative thereof.
<220> FEATURE:
<221> NAME/KEY: MISC_FEATURE
<222> LOCATION: (7)..(7)
<223> OTHER INFORMATION: Xaa is Pro or a derivative thereof.
<220> FEATURE:
<221> NAME/KEY: MISC_FEATURE
<222> LOCATION: (8)..(8)
<223> OTHER INFORMATION: Xaa is Trp or a derivative thereof.

<400> SEQUENCE: 141

Xaa Xaa Xaa Xaa Xaa Xaa Xaa Xaa
1               5

<210> SEQ ID NO 142
<211> LENGTH: 15
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: MISC_FEATURE
<222> LOCATION: (1)..(8)
<223> OTHER INFORMATION: Xaa is any amino acid residue or a derivative
      thereof.
<220> FEATURE:
<221> NAME/KEY: MISC_FEATURE
<222> LOCATION: (9)..(9)
<223> OTHER INFORMATION: Xaa is His or a derivative thereof.
<220> FEATURE:
<221> NAME/KEY: MISC_FEATURE
<222> LOCATION: (10)..(10)
<223> OTHER INFORMATION: Xaa is Pro or a derivative thereof.
<220> FEATURE:
<221> NAME/KEY: MISC_FEATURE
<222> LOCATION: (11)..(15)
<223> OTHER INFORMATION: Xaa is any amino acid residue or a derivative
      thereof.

<400> SEQUENCE: 142

Xaa Xaa Xaa Xaa Xaa Xaa Xaa Xaa Xaa Xaa Xaa Xaa Xaa Xaa Xaa
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: MISC_FEATURE
<222> LOCATION: (2)..(9)
<223> OTHER INFORMATION: Xaa is any amino acid residue or a derivative
      thereof.

<400> SEQUENCE: 143

Phe Xaa Xaa Xaa Xaa Xaa Xaa Xaa Xaa Cys Ser Gly Gly Gly Gly Ser
1               5                   10                  15

<210> SEQ ID NO 144
<211> LENGTH: 51
<212> TYPE: DNA
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (4)..(5)
<223> OTHER INFORMATION: N is any nucleic acid base.
<220> FEATURE:
```

<220> FEATURE:
<221> NAME/KEY: misc_feature
<222> LOCATION: (7)..(8)
<223> OTHER INFORMATION: N is any nucleic acid base.
<220> FEATURE:
<221> NAME/KEY: misc_feature
<222> LOCATION: (10)..(11)
<223> OTHER INFORMATION: N is any nucleic acid base.
<220> FEATURE:
<221> NAME/KEY: misc_feature
<222> LOCATION: (13)..(14)
<223> OTHER INFORMATION: N is any nucleic acid base.
<220> FEATURE:
<221> NAME/KEY: misc_feature
<222> LOCATION: (16)..(17)
<223> OTHER INFORMATION: N is any nucleic acid base.
<220> FEATURE:
<221> NAME/KEY: misc_feature
<222> LOCATION: (19)..(20)
<223> OTHER INFORMATION: N is any nucleic acid base.
<220> FEATURE:
<221> NAME/KEY: misc_feature
<222> LOCATION: (22)..(23)
<223> OTHER INFORMATION: N is any nucleic acid base.
<220> FEATURE:
<221> NAME/KEY: misc_feature
<222> LOCATION: (25)..(26)
<223> OTHER INFORMATION: N is any nucleic acid base.
<220> FEATURE:
<221> NAME/KEY: misc_feature
<222> LOCATION: (28)..(29)
<223> OTHER INFORMATION: N is any nucleic acid base.
<220> FEATURE:
<221> NAME/KEY: misc_feature
<222> LOCATION: (28)..(48)
<223> OTHER INFORMATION: One or more sets of NNK nucleotide bases may be absent.
<220> FEATURE:
<221> NAME/KEY: misc_feature
<222> LOCATION: (31)..(32)
<223> OTHER INFORMATION: N is any nucleic acid base.
<220> FEATURE:
<221> NAME/KEY: misc_feature
<222> LOCATION: (34)..(35)
<223> OTHER INFORMATION: N is any nucleic acid base.
<220> FEATURE:
<221> NAME/KEY: misc_feature
<222> LOCATION: (37)..(38)
<223> OTHER INFORMATION: N is any nucleic acid base.
<220> FEATURE:
<221> NAME/KEY: misc_feature
<222> LOCATION: (40)..(41)
<223> OTHER INFORMATION: N is any nucleic acid base.
<220> FEATURE:
<221> NAME/KEY: misc_feature
<222> LOCATION: (43)..(44)
<223> OTHER INFORMATION: N is any nucleic acid base.
<220> FEATURE:
<221> NAME/KEY: misc_feature
<222> LOCATION: (46)..(47)
<223> OTHER INFORMATION: N is any nucleic acid base.

<400> SEQUENCE: 144
atgnnknnkn nknnknnknn knnknnknnk nnknnknnkn nknnknnktg c            51

<210> SEQ ID NO 145
<211> LENGTH: 51
<212> TYPE: RNA
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (4)..(5)
<223> OTHER INFORMATION: N is any nucleic acid base.
<220> FEATURE:
<221> NAME/KEY: misc_feature
<222> LOCATION: (7)..(8)

```
<223> OTHER INFORMATION: N is any nucleic acid base.
<220> FEATURE:
<221> NAME/KEY: misc_feature
<222> LOCATION: (10)..(11)
<223> OTHER INFORMATION: N is any nucleic acid base.
<220> FEATURE:
<221> NAME/KEY: misc_feature
<222> LOCATION: (13)..(14)
<223> OTHER INFORMATION: N is any nucleic acid base.
<220> FEATURE:
<221> NAME/KEY: misc_feature
<222> LOCATION: (16)..(17)
<223> OTHER INFORMATION: N is any nucleic acid base.
<220> FEATURE:
<221> NAME/KEY: misc_feature
<222> LOCATION: (19)..(20)
<223> OTHER INFORMATION: N is any nucleic acid base.
<220> FEATURE:
<221> NAME/KEY: misc_feature
<222> LOCATION: (22)..(23)
<223> OTHER INFORMATION: N is any nucleic acid base.
<220> FEATURE:
<221> NAME/KEY: misc_feature
<222> LOCATION: (25)..(26)
<223> OTHER INFORMATION: N is any nucleic acid base.
<220> FEATURE:
<221> NAME/KEY: misc_feature
<222> LOCATION: (28)..(29)
<223> OTHER INFORMATION: N is any nucleic acid base.
<220> FEATURE:
<221> NAME/KEY: misc_feature
<222> LOCATION: (28)..(48)
<223> OTHER INFORMATION: One or more sets of NNK nucleotide bases may be
      absent.
<220> FEATURE:
<221> NAME/KEY: misc_feature
<222> LOCATION: (31)..(32)
<223> OTHER INFORMATION: N is any nucleic acid base.
<220> FEATURE:
<221> NAME/KEY: misc_feature
<222> LOCATION: (34)..(35)
<223> OTHER INFORMATION: N is any nucleic acid base.
<220> FEATURE:
<221> NAME/KEY: misc_feature
<222> LOCATION: (37)..(38)
<223> OTHER INFORMATION: N is any nucleic acid base.
<220> FEATURE:
<221> NAME/KEY: misc_feature
<222> LOCATION: (40)..(41)
<223> OTHER INFORMATION: N is any nucleic acid base.
<220> FEATURE:
<221> NAME/KEY: misc_feature
<222> LOCATION: (43)..(44)
<223> OTHER INFORMATION: N is any nucleic acid base.
<220> FEATURE:
<221> NAME/KEY: misc_feature
<222> LOCATION: (46)..(47)
<223> OTHER INFORMATION: N is any nucleic acid base.

<400> SEQUENCE: 145
augnnknnkn nknnknnknn knnknnknnk nnknnknnkn nknnknnkug c          51

<210> SEQ ID NO 146
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: MISC_FEATURE
<222> LOCATION: (1)..(1)
<223> OTHER INFORMATION: Xaa is any amino acid residue.

<400> SEQUENCE: 146

Xaa Val Val Val Ser Thr Asp Pro Trp Val Asn Gly Leu Trp Leu Arg
1               5                   10                  15
```

Cys

<210> SEQ ID NO 147
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 147

Xaa Val Val Val Ser Thr Asp Pro Trp Val Asn Gly Leu Trp Phe Pro
1               5                   10                  15

Cys

<210> SEQ ID NO 148
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 148

Xaa Val Val Val Ser Thr Asp Pro Trp Val Asn Gly Leu Trp Phe Tyr
1               5                   10                  15

Cys

<210> SEQ ID NO 149
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 149

Xaa Val Val Val Ser Thr Asp Pro Trp Val Asn Gly Leu Trp Leu Trp
1               5                   10                  15

Cys

<210> SEQ ID NO 150
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 150

Xaa Val Val Val Ser Thr Asp Pro Trp Val Asn Gly Leu Trp Leu Gln
1               5                   10                  15

Cys

```
<210> SEQ ID NO 151
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 151

Xaa Val Val Val Ser Thr Asp Pro Trp Ala Asn Gly Leu Trp Leu Ala
1               5                   10                  15

Cys

<210> SEQ ID NO 152
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 152

Xaa Val Val Val Ser Thr Asp Pro Trp Val Asn Gly Leu Tyr Leu Asp
1               5                   10                  15

Cys

<210> SEQ ID NO 153
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 153

Xaa Val Val Arg His Thr Asp Pro Trp Val Asn Gly Leu Tyr Ile Asp
1               5                   10                  15

Cys

<210> SEQ ID NO 154
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 154

Xaa Val Val Val His Thr Asp Pro Trp Val Asn Gly Leu Tyr Ile Asp
1               5                   10                  15

Cys

<210> SEQ ID NO 155
<211> LENGTH: 17
```

```
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 155

Xaa Val Val Arg His Asn Asp Pro Trp Val Asn Gly Leu Tyr Ile Asp
1               5                   10                  15
Cys

<210> SEQ ID NO 156
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 156

Xaa Val Val Ser His Pro Asp Pro Trp Val Asn Gly Leu Tyr Ile Asp
1               5                   10                  15
Cys

<210> SEQ ID NO 157
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 157

Xaa Val Val Ser His His Asp Pro Trp Val Asn Gly Leu Tyr Ile Asp
1               5                   10                  15
Cys

<210> SEQ ID NO 158
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 158

Xaa Val Val Lys His Ser Asp Pro Trp Val Asn Gly Leu Tyr Ile Asp
1               5                   10                  15
Cys

<210> SEQ ID NO 159
<211> LENGTH: 17
<212> TYPE: PRT
<213> ORGANISM: Artificial Sequence
<220> FEATURE:
```

<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 159

Xaa Val Val Lys His Pro Asp Pro Trp Val Asn Gly Leu Tyr Ile Asp
1               5                   10                  15

Cys

<210> SEQ ID NO 160
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 160

Xaa Ile Val Arg His Pro Asp Pro Trp Val Asn Gly Leu Tyr Ile Asp
1               5                   10                  15

Cys

<210> SEQ ID NO 161
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 161

Xaa Ile Val Thr His Ser Asp Pro Trp Val Asn Gly Leu Tyr Ile Asp
1               5                   10                  15

Cys

<210> SEQ ID NO 162
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 162

Xaa Val Val Thr His Ser Asp Pro Trp Val Asn Gly Leu Tyr Ile Asp
1               5                   10                  15

Cys

<210> SEQ ID NO 163
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature

```
<222> LOCATION: (1)..(1)
<223> OTHER INFORMATION: Xaa can be any naturally occurring amino acid

<400> SEQUENCE: 163

Xaa Thr Val Thr His Thr Asp Pro Trp Val Asn Gly Leu Tyr Ile Asp
1               5                   10                  15
Cys

<210> SEQ ID NO 164
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 164

Xaa Thr Val Lys His Thr Asp Pro Trp Val Asn Gly Leu Tyr Ile Asp
1               5                   10                  15
Cys

<210> SEQ ID NO 165
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 165

Xaa Thr Val Arg His Thr Asp Pro Trp Val Asn Gly Leu Tyr Ile Asp
1               5                   10                  15
Cys

<210> SEQ ID NO 166
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 166

Xaa Thr Val Tyr His Ser Asp Pro Trp Val Asn Gly Leu Tyr Ile Asp
1               5                   10                  15
Cys

<210> SEQ ID NO 167
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid
```

<400> SEQUENCE: 167

Xaa Val Val Val Ser Thr Asp Pro Trp Val Asn Gly Leu Tyr Leu Asp
1               5                   10                  15

Cys

<210> SEQ ID NO 168
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 168

Xaa Thr Val Ser His Pro Asp Pro Trp Val Asn Gly Leu Trp Ile Arg
1               5                   10                  15

Cys

<210> SEQ ID NO 169
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 169

Xaa Thr Val Tyr His Pro Asp Pro Trp Val Asn Gly Leu Trp Ile Arg
1               5                   10                  15

Cys

<210> SEQ ID NO 170
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 170

Xaa Thr Val Trp His Pro Asp Pro Trp Val Asn Gly Leu Trp Ile Tyr
1               5                   10                  15

Cys

<210> SEQ ID NO 171
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 171

Xaa Glu Val Lys His Pro Asp Pro Trp Val Asn Gly Leu Trp Ile Tyr

```
1               5                   10                  15
Cys

<210> SEQ ID NO 172
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 172

Xaa Thr Val Val His Pro Asp Pro Trp Val Asn Gly Leu Trp Ile Ser
1               5                   10                  15

Cys

<210> SEQ ID NO 173
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 173

Xaa Thr Val Arg His Pro Asp Pro Trp Val Asn Gly Leu Trp Leu Ser
1               5                   10                  15

Cys

<210> SEQ ID NO 174
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 174

Xaa Thr Val Arg His Pro Asp Pro Trp Val Asn Gly Leu Trp Phe Ser
1               5                   10                  15

Cys

<210> SEQ ID NO 175
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 175

Xaa Thr Val Ser His Pro Asp Pro Trp Val Asn Gly Leu Trp Leu Gln
1               5                   10                  15

Cys
```

```
<210> SEQ ID NO 176
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 176

Xaa Thr Val Thr His Pro Asp Pro Trp Val Asn Gly Leu Trp Leu Pro
1               5                   10                  15

Cys

<210> SEQ ID NO 177
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 177

Xaa Thr Val Thr His Pro Asp Pro Trp Val Asn Gly Leu Tyr Leu Pro
1               5                   10                  15

Cys

<210> SEQ ID NO 178
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 178

Xaa Thr Val Tyr His Pro Asp Pro Trp Val Asn Gly Leu Trp Leu Pro
1               5                   10                  15

Cys

<210> SEQ ID NO 179
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 179

Xaa Thr Val Val His Pro Asp Pro Trp Val Asn Gly Leu Trp Leu Pro
1               5                   10                  15

Cys

<210> SEQ ID NO 180
```

```
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 180

Xaa Thr Val Phe His Pro Asp Pro Trp Val Asn Gly Leu Trp Ile Pro
1               5                   10                  15

Cys

<210> SEQ ID NO 181
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 181

Xaa Ala Val Thr His Ser Asp Pro Trp Val Asn Gly Leu Trp Leu Pro
1               5                   10                  15

Cys

<210> SEQ ID NO 182
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 182

Xaa Thr Val Thr His Ser Asp Pro Trp Val Asn Gly Leu Trp Phe Pro
1               5                   10                  15

Cys

<210> SEQ ID NO 183
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 183

Xaa Glu Val Ser His Pro Asp Pro Trp Val Asn Gly Leu Trp Phe Pro
1               5                   10                  15

Cys

<210> SEQ ID NO 184
<211> LENGTH: 17
<212> TYPE: PRT
<213> ORGANISM: Artificial Sequence
```

<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 184

Xaa Ala Val Ser His Pro Asp Pro Trp Val Asn Gly Leu Trp Phe Pro
1               5                   10                  15
Cys

<210> SEQ ID NO 185
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 185

Xaa Ser Val Val His His Asp Pro Trp Val Asn Gly Leu Trp Phe Pro
1               5                   10                  15
Cys

<210> SEQ ID NO 186
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 186

Xaa Val Val Val Ser Thr Asp Pro Trp Val Asn Gly Leu Tyr Leu Asp
1               5                   10                  15
Cys

<210> SEQ ID NO 187
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 187

Xaa Ile Gly His Tyr Arg Val Lys Val His Pro Ile Ser Leu Ala Pro
1               5                   10                  15
Cys

<210> SEQ ID NO 188
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:

```
<221> NAME/KEY: misc_feature
<222> LOCATION: (1)..(1)
<223> OTHER INFORMATION: Xaa can be any naturally occurring amino acid

<400> SEQUENCE: 188

Xaa Ile Gly Arg Tyr Arg Val Lys Val His Pro Ile Ser Leu Ala Pro
1               5                   10                  15

Cys

<210> SEQ ID NO 189
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 189

Xaa Ile Gly His Tyr Arg Val Lys Val His Pro Ile Ser Leu Ser Pro
1               5                   10                  15

Cys

<210> SEQ ID NO 190
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 190

Xaa Ile Gly Pro Tyr Arg Val Lys Val His Pro Ile Ser Leu Glu Pro
1               5                   10                  15

Cys

<210> SEQ ID NO 191
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 191

Xaa Ile Gly His Tyr Arg Val Lys Val His Pro Ile Ser Leu Glu Pro
1               5                   10                  15

Cys

<210> SEQ ID NO 192
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid
```

<400> SEQUENCE: 192

Xaa Ile Gly His Tyr Arg Val Lys Val His Pro Ile Ser Leu Glu Tyr
1               5                   10                  15

Cys

<210> SEQ ID NO 193
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 193

Xaa Ile Gly His Tyr Arg Val Lys Val His Pro Ile Ser Leu Glu Trp
1               5                   10                  15

Cys

<210> SEQ ID NO 194
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 194

Xaa Ile Gly His Tyr Arg Val Lys Val His Pro Ile Ser Leu Leu Pro
1               5                   10                  15

Cys

<210> SEQ ID NO 195
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 195

Xaa Ile Gly His Tyr Arg Val Lys Val His Pro Val Ser Leu Glu Pro
1               5                   10                  15

Cys

<210> SEQ ID NO 196
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 196

```
Xaa Ile Gly His Tyr Arg Val Lys Val His Pro Val Ser Phe Glu Pro
1               5                   10                  15

Cys

<210> SEQ ID NO 197
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 197

Xaa Ile Gly His Tyr Arg Val Lys Val His Pro Val Ser Leu Glu Ser
1               5                   10                  15

Cys

<210> SEQ ID NO 198
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 198

Xaa Ile Gly Asp Tyr Arg Val Lys Val His Pro Val Ser Leu Glu Tyr
1               5                   10                  15

Cys

<210> SEQ ID NO 199
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 199

Xaa Ile Gly His Tyr Arg Val Lys Val His Pro Val Thr Leu Ala Trp
1               5                   10                  15

Cys

<210> SEQ ID NO 200
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 200

Xaa Val Gly His Tyr Arg Val Lys Val His Pro Val Gly Leu Trp Pro
1               5                   10                  15
```

Cys

<210> SEQ ID NO 201
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 201

Xaa Ile Gly His Tyr Arg Val Lys Val His Pro Ile Ser Leu Glu Arg
1               5                   10                  15

Cys

<210> SEQ ID NO 202
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 202

Xaa Val Asn Gly Tyr Arg Val Lys Val His Pro Ile Ser Leu Glu Arg
1               5                   10                  15

Cys

<210> SEQ ID NO 203
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 203

Xaa Val Asn Gly Tyr Ser Ile Lys Val His Pro Ile Ser Leu Glu Arg
1               5                   10                  15

Cys

<210> SEQ ID NO 204
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 204

Xaa Ile Asn Gly Tyr Lys Ile Lys Val His Pro Ile Ser Leu Glu Arg
1               5                   10                  15

Cys

```
<210> SEQ ID NO 205
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 205

Xaa Ile Gly Pro Tyr Lys Ile Arg Val His Pro Ile Ser Leu Glu Arg
1               5                   10                  15

Cys

<210> SEQ ID NO 206
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 206

Xaa Ile Gly Pro Tyr Arg Ile Arg Leu His Pro Ile Ser Leu Glu Arg
1               5                   10                  15

Cys

<210> SEQ ID NO 207
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 207

Xaa Tyr Gly Pro Tyr Ala Ile Lys Val His Pro Ile Ser Leu Glu Arg
1               5                   10                  15

Cys

<210> SEQ ID NO 208
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 208

Xaa Ile Gly Pro Tyr Val Ile Lys Val His Pro Ile Ser Leu Glu Arg
1               5                   10                  15

Cys

<210> SEQ ID NO 209
<211> LENGTH: 17
<212> TYPE: PRT
```

```
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 209

Xaa Ile Gly Arg Phe Arg Ile Lys Val His Pro Ile Ser Leu Glu Arg
1               5                   10                  15

Cys

<210> SEQ ID NO 210
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 210

Xaa Leu Gly Arg Trp Ser Ile Lys Val His Pro Ile Ser Leu Glu Arg
1               5                   10                  15

Cys

<210> SEQ ID NO 211
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 211

Xaa Ile Gly Ser Phe Val Ile Arg Val His Pro Ile Ser Leu Glu Arg
1               5                   10                  15

Cys

<210> SEQ ID NO 212
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 212

Xaa Ile Arg Gly Phe Arg Ile Arg Val His Pro Ile Ser Leu Glu Arg
1               5                   10                  15

Cys

<210> SEQ ID NO 213
<211> LENGTH: 17
<212> TYPE: PRT
<213> ORGANISM: Artificial Sequence
<220> FEATURE:
<223> OTHER INFORMATION: VEGFR2 inhibitor peptide
```

<220> FEATURE:
<221> NAME/KEY: misc_feature
<222> LOCATION: (1)..(1)
<223> OTHER INFORMATION: Xaa can be any naturally occurring amino acid

<400> SEQUENCE: 213

Xaa Val Gly Pro Tyr Arg Ile Arg Val His Pro Ile Ser Leu Glu Arg
1               5                   10                  15
Cys

<210> SEQ ID NO 214
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 214

Xaa Val Gly Ile Tyr Gln Ile Arg Val His Pro Ile Ser Leu Glu Arg
1               5                   10                  15
Cys

<210> SEQ ID NO 215
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 215

Xaa Ile Gly His Tyr Arg Val Lys Val His Pro Val Ser Leu Glu Tyr
1               5                   10                  15
Cys

<210> SEQ ID NO 216
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 216

Xaa Ile Gly His Tyr Arg Val Lys Val His Pro Ile Ser Leu Glu Arg
1               5                   10                  15
Cys

<210> SEQ ID NO 217
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)

```
<223> OTHER INFORMATION: Xaa can be any naturally occurring amino acid

<400> SEQUENCE: 217

Xaa Leu Tyr Gly Tyr Arg Val Lys Val His Pro Ile Ser Leu Glu Pro
1               5                   10                  15

Cys

<210> SEQ ID NO 218
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 218

Xaa Ile Gly Ile Tyr Arg Val Lys Val His Pro Ile Ser Leu Glu Pro
1               5                   10                  15

Cys

<210> SEQ ID NO 219
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 219

Xaa Ile Gly Pro Tyr Arg Val Lys Val His Pro Ile Ser Leu Glu Pro
1               5                   10                  15

Cys

<210> SEQ ID NO 220
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 220

Xaa Ile Gly Pro Tyr Trp Val Lys Val His Pro Ile Ser Leu Glu Pro
1               5                   10                  15

Cys

<210> SEQ ID NO 221
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 221
```

```
Xaa Ile Gly Pro Tyr Arg Val Lys Val His Pro Val Ser Leu Glu Pro
1               5                   10                  15

Cys

<210> SEQ ID NO 222
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 222

Xaa Ile Gly Pro Tyr Arg Ile Lys Val His Pro Val Ser Leu Glu Pro
1               5                   10                  15

Cys

<210> SEQ ID NO 223
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 223

Xaa Val Gly Pro Tyr Arg Val Lys Val His Pro Val Ser Leu Glu Pro
1               5                   10                  15

Cys

<210> SEQ ID NO 224
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 224

Xaa Ile Gly Pro Tyr Val Val Lys Val His Pro Val Ser Leu Glu Pro
1               5                   10                  15

Cys

<210> SEQ ID NO 225
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 225

Xaa Ile Gly Pro Tyr Arg Val Lys Val His Pro Val Ser Leu Glu Tyr
1               5                   10                  15
```

Cys

<210> SEQ ID NO 226
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 226

Xaa Ile Gly Pro Tyr Trp Val Lys Val His Pro Val Ser Leu Glu Trp
1               5                   10                  15

Cys

<210> SEQ ID NO 227
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 227

Xaa Ile Asn Gly Tyr Tyr Val Lys Val His Pro Val Ser Leu Asp Trp
1               5                   10                  15

Cys

<210> SEQ ID NO 228
<211> LENGTH: 17
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 228

Xaa Ile Gly His Tyr Arg Val Lys Val His Pro Ile Ser Leu Glu Arg
1               5                   10                  15

Cys

<210> SEQ ID NO 229
<211> LENGTH: 7
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: MISC_FEATURE
<222> LOCATION: (1)..(1)
<223> OTHER INFORMATION: Xaa is any amino acid residue or a derivative
      thereof.
<220> FEATURE:
<221> NAME/KEY: MISC_FEATURE
<222> LOCATION: (2)..(2)
<223> OTHER INFORMATION: Xaa is Asn or a derivative thereof.
<220> FEATURE:
<221> NAME/KEY: MISC_FEATURE
<222> LOCATION: (3)..(3)

-continued

```
<223> OTHER INFORMATION: Xaa is Gly or a derivative thereof.
<220> FEATURE:
<221> NAME/KEY: MISC_FEATURE
<222> LOCATION: (4)..(4)
<223> OTHER INFORMATION: Xaa is Leu or a derivative thereof.
<220> FEATURE:
<221> NAME/KEY: MISC_FEATURE
<222> LOCATION: (5)..(7)
<223> OTHER INFORMATION: Xaa is any amino acid residue or a derivative
      thereof.

<400> SEQUENCE: 229

Xaa Xaa Xaa Xaa Xaa Xaa Xaa
1               5

<210> SEQ ID NO 230
<211> LENGTH: 8
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: MISC_FEATURE
<222> LOCATION: (1)..(8)
<223> OTHER INFORMATION: Xaa is any amino acid residue or a derivative
      thereof.

<400> SEQUENCE: 230

Xaa Xaa Xaa Xaa Xaa Xaa Xaa Xaa
1               5

<210> SEQ ID NO 231
<211> LENGTH: 7
<212> TYPE: PRT
<213> ORGANISM: Artificial Sequence
<220> FEATURE:
<223> OTHER INFORMATION: VEGFR2 inhibitor peptide
<220> FEATURE:
<221> NAME/KEY: MISC_FEATURE
<222> LOCATION: (1)..(1)
<223> OTHER INFORMATION: Xaa is His or a derivative thereof.
<220> FEATURE:
<221> NAME/KEY: MISC_FEATURE
<222> LOCATION: (2)..(2)
<223> OTHER INFORMATION: Xaa is Pro or a derivative thereof.
<220> FEATURE:
<221> NAME/KEY: MISC_FEATURE
<222> LOCATION: (3)..(7)
<223> OTHER INFORMATION: Xaa is any amino acid residue or a derivative
      thereof.

<400> SEQUENCE: 231

Xaa Xaa Xaa Xaa Xaa Xaa Xaa
1               5

<210> SEQ ID NO 232
<211> LENGTH: 18
<212> TYPE: PRT
<213> ORGANISM: Artificial Sequence
<220> FEATURE:
<223> OTHER INFORMATION: Peptide prepared by solid-phase synthesis.
<220> FEATURE:
<221> NAME/KEY: MISC_FEATURE
<222> LOCATION: (18)..(18)
<223> OTHER INFORMATION: Resin attached to C-terminus.

<400> SEQUENCE: 232

Phe Val Val Val Ser Thr Asp Pro Trp Val Asn Gly Leu Tyr Ile Asp
1               5                   10                  15

Cys Gly
```

```
<210> SEQ ID NO 233
<211> LENGTH: 16
<212> TYPE: PRT
<213> ORGANISM: Artificial Sequence
<220> FEATURE:
<223> OTHER INFORMATION: Peptide BL1 prepared by solid-phase synthesis.
<220> FEATURE:
<221> NAME/KEY: MISC_FEATURE
<222> LOCATION: (16)..(16)
<223> OTHER INFORMATION: Resin attached to C-terminus.

<400> SEQUENCE: 233

Phe Ile Gly His Tyr Arg Val His Pro Ile Ser Leu Glu Arg Cys Gly
1               5                   10                  15
```